United States Patent
Naidu

(10) Patent No.: US 7,326,775 B2
(45) Date of Patent: *Feb. 5, 2008

(54) TREATMENTS FOR CONTAMINANT REDUCTION IN LACTOFERRIN PREPARATIONS AND LACTOFERRIN-CONTAINING COMPOSITIONS

(75) Inventor: A. Satanarayan Naidu, Diamond Bar, CA (US)

(73) Assignee: en-N-tech, Inc., Pomona, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/293,565

(22) Filed: Dec. 2, 2005

(65) Prior Publication Data

US 2006/0093594 A1    May 4, 2006

Related U.S. Application Data

(62) Division of application No. 11/072,054, filed on Mar. 3, 2005, now Pat. No. 7,125,963.

(60) Provisional application No. 60/549,998, filed on Mar. 3, 2004.

(51) Int. Cl.
  C07K 14/00   (2006.01)
  A61K 38/16   (2006.01)

(52) U.S. Cl. ............. 530/400; 530/350; 530/395; 514/8; 514/6; 424/9.1; 424/85.1

(58) Field of Classification Search ............ 514/8, 514/6; 530/350, 395, 400; 424/85.1, 9.1
See application file for complete search history.

(56) References Cited

U.S. PATENT DOCUMENTS

| | | |
|---|---|---|
| 4,436,658 A | 3/1984 | Peyrouset et al. |
| 4,518,696 A | 5/1985 | Gehrman et al. |
| 4,591,499 A | 5/1986 | Linn et al. |
| 4,668,771 A | 5/1987 | Kawakami et al. |
| 4,791,193 A | 12/1988 | Okonogi et al. |
| 4,997,914 A | 3/1991 | Kawakami et al. |
| 5,149,647 A | 9/1992 | Burling |
| 5,156,875 A | 10/1992 | Monte |
| 5,179,197 A | 1/1993 | Uchida et al. |
| 5,206,156 A | 4/1993 | Samain et al. |
| 5,214,028 A | 5/1993 | Tomita et al. |
| 5,240,909 A | 8/1993 | Nitsche |
| 5,296,464 A | 3/1994 | Tomita et al. |
| 5,389,611 A | 2/1995 | Tomita et al. |
| 5,516,675 A | 5/1996 | Uchida et al. |
| 5,543,392 A | 8/1996 | Tomita et al. |
| 5,571,896 A | 11/1996 | Conneely et al. |
| 5,596,082 A | 1/1997 | Kussendrager et al. |
| 5,606,086 A | 2/1997 | Dosako et al. |
| 5,656,268 A | 8/1997 | Sorodsky |
| 5,756,680 A | 5/1998 | Ahmed et al. |
| 5,834,424 A | 11/1998 | Valenti et al. |
| 5,849,885 A | 12/1998 | Nuyens et al. |
| 5,861,491 A | 1/1999 | Nuijens et al. |
| 5,869,446 A | 2/1999 | Valenti et al. |
| 5,895,648 A | 4/1999 | Vesely et al. |
| 5,919,913 A | 7/1999 | Nuyens et al. |
| 5,922,375 A | 7/1999 | Luchansky et al. |
| 5,955,086 A | 9/1999 | DeLuca et al. |
| 6,010,698 A | 1/2000 | Kussendrager et al. |
| 6,066,469 A | 5/2000 | Kruzel et al. |
| 6,080,559 A | 6/2000 | Conneely et al. |
| 6,093,394 A | 7/2000 | Chrisope |
| 6,140,355 A | 10/2000 | Egidio et al. |
| 6,172,040 B1 | 1/2001 | Naidu |
| 6,268,487 B1 | 7/2001 | Kutzko et al. |
| 6,306,391 B1 | 10/2001 | Modi et al. |
| 6,333,311 B1 | 12/2001 | Nuijens et al. |
| 6,372,209 B1 | 4/2002 | Chrisope |
| 6,399,570 B1 | 6/2002 | Mann |
| 6,436,453 B1 | 8/2002 | van Lengerich et al. |
| 6,475,511 B2 | 11/2002 | Gohlke et al. |

(Continued)

FOREIGN PATENT DOCUMENTS

EP    0271364 B1    9/1992

(Continued)

OTHER PUBLICATIONS

Aeschbach R et al., Antioxidant actions of thymol, carvacrol, 6-gingerol, zingerone and hydroxytyrosol. Food Chem Toxicol 32:31-6, 1994.

(Continued)

*Primary Examiner*—Chih-Min Kam
(74) *Attorney, Agent, or Firm*—Louis C. Cullman; Kirkpatrick & Lockhart Preston Gates Ellis LLP

(57) ABSTRACT

A method of preparing an ultra-cleansed lactoferrin preparation, termed treatment for contaminant reduction (TCR) is provided which includes the steps of treating commercial lactoferrin preparation with at least one each of surfactants, antioxidants and polyphenols to form purified lactoferrin (LF-TCR) and drying the LF-TCR. Additionally a therapeutic lactoferrin composition is provided which contains LF-TCR and optionally surfactants, antioxidants, polyphenols, tissue/membrane diffusion facilitating agents and anionic compounds. The therapeutic lactoferrin composition can additionally contain bioactive agents, dietary supplements, nutraceuticals/functional foods, prophylactic agents, therapeutic agents and probiotic lactic acid bacteria.

10 Claims, 2 Drawing Sheets

U.S. PATENT DOCUMENTS

| | | | |
|---|---|---|---|
| 7,125,963 B2* | 10/2006 | Naidu | 530/400 |
| 2001/0001711 A1 | 5/2001 | Olshenitsky et al. | |
| 2002/0004073 A1 | 1/2002 | Gohlke et al. | |
| 2002/0048567 A1 | 4/2002 | Olshenitsky et al. | |
| 2002/0081311 A1 | 6/2002 | Shanahan et al. | |
| 2002/0090365 A1 | 7/2002 | Chrisope | |
| 2002/0094328 A1 | 7/2002 | De Simone | |
| 2002/0119237 A1 | 8/2002 | Hevey | |
| 2003/0003059 A1* | 1/2003 | Dana | 424/49 |
| 2004/0043922 A1 | 3/2004 | Naidu | |

FOREIGN PATENT DOCUMENTS

| | | |
|---|---|---|
| EP | 0568200 A2 | 3/1993 |
| EP | 0753308 A2 | 1/1997 |
| EP | 0753309 A2 | 1/1997 |
| WO | 91/13982 | 9/1991 |
| WO | 93/01823 | 2/1993 |
| WO | 98/55131 | 12/1998 |
| WO | 00/72690 A2 | 12/2000 |
| WO | 00/72874 A1 | 12/2000 |
| WO | 01/11077 A2 | 2/2001 |

OTHER PUBLICATIONS

Alugupalli, K.R. et al. Lactoferrin Interaction with *Actinobacillus actinomycetermcomitans*. Oral Micro. Immunol., 10:35-41, 1995.

Alugupalli, K.R. et al. Effect of Lactoferrin on Interaction of Prevotella intermedia with Plasma and Subepithelial Matrix Proteins. Oral Microbiol Immunol, 9:174-179, 1994.

Appelmelk BJ et al., Lactoferrin is a lipid A binding protein. Infect Immun 62:2628-2632, 1994.

Axelsson L, Lactic acid bacterial—classification and physiology. In 'Lactic acid bacteria—microbiology and functional aspects', ed. S Salminen, pp. 1-72. New York: Marcel Dekker, 1998.

Bennett RM et al., Calcium-dependant polymerization of lactoferrin. Biochem Biophys Res Commun 101:88-95, 1981.

Benzie IF, Strain JJ, Ferric reducing/antioxidant power assay: direct measure of total antioxidant activity of biological fluids and modified version for simultaneous measurement of total antioxidant power and ascorbic acid concentration. In: 'Methods in Enzymology: Oxidants and Antioxidants', et. L/ Packer, pp. 15-27, Orlando, FL, Academic Press, 1999.

Bhat VB, Madyastha KM, Scavenging of peroxynitrite by phycocyanin and phycocyanobilin from *Spirulina platensis*—protection against oxidative damage to DNA. Biochem Biophys Res Comm 285:262-6, 2001.

Bors W et al., Flavonoids and phytophenols—chemistry and biology. In 'Handbook of Antioxidants', ed. Cadenas E, Packer L, pp. 409-466. New York: Marcel Dekker, 1996.

Burrin DG et al., Orally administered lactoferrin increases hepatic protein synthesis in formula-fed newborn pigs. Pediatr Res 40:72-6, 1996.

Caccavo D et al., Antimicrobial and immunoregulatory functions of lactoferrin and its potential therapeutic applications. J Endotoxin Res 8:403-17, 2002.

Chan MM et al., Effects of three dietary phytochemicals from tea, rosemary and tumeric on inflammation-induced nitrite production. Cancer Lett 96:23-29, 1995.

Cheynier V, Rigaud J, HPLC separation and characterization of flavonols in the skins of *Vitis vinfera* var. *cinault*. Am J Enol Vitic 37:248-52, 1986.

Cho, Jin-Kook et al., Purification of Membrane-bound Lactoferrin from the Human Milk Fat Globule Membrane, Biosci. Biotechnol. Biochem., 64: 633-635, 2000.

Conway P, Selection criteria for probiotic microorganisms. Asia Pacific J Clin Nutr 5:10-14, 1996.

Cox TM, et al., Iron-binding proteins and influx of iron across the duodenal brush border. Evidence for specific lactotransferrin receptors in the human small intestine. Biochem Biophys Acta 588:120-8, 1979.

Crosa JH, Genetics and molecular biology of siderophore-mediated iron transport in bacteria. Microbiol. Rev. 53:517-30, 1989.

Davidson PM, Naidu AS Phytophenols, In 'Natural Food Antimicrobial Systems', ed. AS Naidu, pp. 265-294. Boca Raton: CRC Press, 2000.

Debbabi H et al., Bovine lactoferrin induces both mucosal and system immune responses in mice. J Dairy Res 65:283-93, 1998.

Elass-Rochard E et al., Lactoferrin-lipopolysaccharide interaction: involvement of the 28-34 loop region of human lactoferrin in the high-affinity binding to *E. coli* 055B5 lipopolysaccharide. Biochem J 312:839-45, 1995.

Erdei, J. et al. Lactoferrin Binds to Porins OmpF and OmpC in *Escherichia coli*. Infect. Immunity, , 62:1236-1240, 1994.

Erridge C et al., Structure and function of lipopolysaccharides. Microbes Infect 4:837-51, 2002.

Fuda, E. et al. Recovery of Lactoferrin and Lactoperoxidase from Sweet Whey Using Colloidal Gas Aphrons (CGAs) Generated from an Anionic Surfactant, AOT. Biotechnol. Progr., 20:514-525, 2004.

Fuller, R. et al. Modification of the Intestinal Microflora Using Probiotics and Prebiotics. Scand . J. Gastroenterol. 32 Suppl:28-31, 1997.

Gadó, et al. Correlation Between Human Lactoferrin Binding and Colicin Susceptibility in *Escherichia coli*. Antimicrobial Agents Chemo., 35: 2538-2543, 1991.

Gemma C et al., Diets enriched in foods with high antioxidant activity reverse age-induced decreases in cerebellar beta-adrenergic function and increases in proinflammatory cytokines. J Neurosci 22:6114-20, 2002.

Gibson, G.R. et al. Dietary Modulation of the Human Colonic Microbiota: Introducing the Concept of Prebiotics. J. Nutr. 125:1401-1412, 1995.

Gibson, G.R. et al. Probiotics and Intestinal Infections. In, Probiotics 2: Applications and Practical Aspects, R. Fuller, ed. Chapman & Hall, pp. 10-39, 1997.

Griffiths, E. et. al. In Vitro Growth Responses of Bifidobacteria and Enteropathogens to Bovine and Human Lactoferrin. Digest. Dis. Sci., 48:1324-1332, 2003.

Harmon RJ et al., Changes in lactoferrin, immunoglobulin G, bovine serum albumin, and α-lactalbumin during acute experimental and natural coliform mastitis in cows. Infect Immun 13:533-42, 1976.

Harper, J.W. et al. Dairy Technology and Engineering, Avi Publishing Co., Inc., Westport, pp. 20-37, 1976.

Havenaar R et al., Selection of strains for probiotic use, p. 209-224. In R. Fuller (ed), Probiotics the scientific basis, Chapman & Hall, London, UK, 1992.

Kalfas S. et al., Human Lactoferrin Binding to Porphyromonas Gingivalis, *Prevotella intermedia* and *Prevotella melaninogenica*. Oral Microbiol. Immunol. 6:350-355, 1991.

Kalfas S. et al. Laminin Binding to *Prevotella intermedia*, Oral Microbiol Immunol, 1992, vol. 7, pp. 235-239.

Kandler O, Weiss N, Regular, nonsporing Gram-positive rods. In 'Bergey's Manual of Systematic Bacteriology', ed. Sneath PHA et al., pp. 1208-1234. Baltimore, Williams and Wilkins, 1986.

Kawakami H, Lonnerdal B, Isolation and function of a receptor for human lactoferrin in human fetal intestinal brush-border membranes. Am J Physiol 261:G841-6, 1991.

Kishore, A.R. et al. Detection of Bacterial Interaction with Lactoferrin by an Enzyme-Linked Ligand Binding Assay (ELBA). J. Med. Microbiol., 37:341-345, 1992.

Kishore, A.R. et al. Specific Binding of Lactoferrin to *Aeromonas hydrophila*. FEMS Microbiol. Lett. 83:115-120, 1991.

Lee WJ et al., The protective effects of lactoferrin feeding against endotoxin lethal shock in germfree piglets. Infect Immun 66:1421-6, 1998.

Liepke C et al., Human milk provides peptides highly stimulating the growth of bifidobacteria. Eur. J. Biochem. 269:712-8, 2002.

Lin HY et al., Inhibition of lipopolysaccharide-induced nitric oxide production by flavonoids in RAW264.7 macrophages involves heme oxygenase-1. Biochem Pharmacol 66:1821-32, 2003.

Lonnerdal B, Trace element absorption in infants as a foundation to setting upper limits for trace elements in infant formulas. J Nutr Suppl 119:1839-44, 1989.

Lönnerdal, B. Nutritional and Physiological Significance of Human Milk Proteins. Am. J. Clin. Nutr. 77:1537S-1543S, 2003.

Lygren, B. et al. Examination of the Immunomodulatory Properties and the Effect on Disease Resistance of Dietary Bovine Lactoferrin and Vitamin C Fed to Atlantic Salmon (*Salmo salar*) for as Short-Term Period. Fish Shellfish Immunol., 9:95-107, 1999.

Majde JA, Microbial cell-wall contaminants in peptides—a potential source of physiological artifacts. Peptides 14:629-32, 1993.

Miller-Catchpole R et al., Lactoferrin can supply iron for the growth of *Bifidobacterium breve*. Natr Res 17:205-13, 1997.

Mitsuoka T, Taxonomy & ecology of bifidobacteria. Bifidobacteria Microflora 3:11-28, 1984.

Miyazawa K et al., Lactoferrin-lipopolysaccharide interactions. J Immunol 146:723-9, 1991.

Morikawa T et al., Potent protective effects of sesquiterpenes and curcumin from *Zedoariae rhizoma* on liver injury induced by D-galactosamine/lipopolysaccharide or TNF-α. Biol Pharm Bull 25:627-31, 2002.

Naidu, A.S. et al. Flavonoids, In : Natural Food Antimicrobial Systems. A.S. Naidu, ed., CRC Press, Boca Raton, pp. 326-348, 2000.

Nichols BL et al., Iron is not required in the lactoferrin stimulation of thymidine incorporation into the DNA of rat crypt enterocytes. Pediatr Res 27:525-8, 1990.

Opal SM, The clinical relevance of endotoxin in human sepsis—a critical analysis. J. Endotoxin Res. 8:473-6, 2002.

Patil CS et al., Protective effects of flavonoids against aging- and lipopolysaccharide-induced cognitive impairment in mice. Pharmacology 69:59-67, 2003.

Paulsson, M. et al. Thermal behavior of bovine lactoferrin in water and its relation to bacterial interaction and antibacterial activity. J. Dairy Science, 76:3711-3720, 1993.

Petschow BW et al., Ability of lactoferrin to promote the growth of *Bifidobacterium* spp. in vitro is independant of receptor binding capacity and iron-saturation levels. J Med Microbiol 48:541-9, 1999.

Raetz CR, Whitfield C, Lipopolysaccharide endotoxins. Annu Rev Biochem 71:635-700, 2002.

Roberts AK et al., Supplementation of an adapted formula with bovine lactoferrin—effects on the infant faecal flora. Acta Paediatr 81:119-24, 1992.

Rosa G, Trugo NM, Iron uptake from lactoferrin by intestinal brush-border membrane vesicles of human neonates. Braz J Med Biol Res 27:1527-31, 1994.

Rylander R, Endotoxin in the environment-exposure and effects. J Endotox Res 8:241-52, 2002.

Salminen, S. et al. Clinical uses of probiotics for stabilizing the gut mucosal barrier: successful strains and future challenges. Antone van Leewenhoek 70:247-358, 1996.

Sato N et al., Lactoferrin inhibits *Bacillus cereus* growth and heme analogs recover its growth. Biol Pharm Bull 22:197-9, 1999.

Shau et al., Modulation of natural killer and lymphokine-activated killer cell cytotoxicity by lactoferrin. J Leukoc Biol 51:343-9, 1992.

Tabak L et al., Changes in lactoferrin and other proteins in a case of recurrent parotitis. J Oral Pathol 7:91-9, 1978.

Teraguchi S et al., Bacteriostatic effect of orally administered bovine lactoferrin on proliferation of Clostridium species in the gut of mice fed bovine milk. Appl Environ Microbiol 61:501-6, 1995.

Teraguchi S et al., Orally administered bovine lactoferrin inhibits bacteria translocation in mice fed bovine milk. Appl Environ Microbiol 61:4131-4, 1995.

Tigyi, Z. et al. Lactoferrin-binding proteins in *Shigella flexneri*. Infect. Immun., 60:2619-2626, 1992.

Tuomola, E.M. et al. The effect of probiotic bacteria on the adhesion of pathogens to human intestinal mucus. FEMS Immunol. Med. Micro., 26:137-142, 1999.

Tuomola, E.M. et al. Adhesion of some probiotic and dairy Lactobacillus strains to Caco-2 cell cultures. Int. J. Food Micro. 41:45-51, 1998.

Vanderhoof JA et al., Treatment strategies for small bowel bacterial overgrowth in short bowel syndrome. J Pediatr Gastroenterol Nutr 27:155-60, 1998.

Visioli F. et al., Free radical-scavenging properties of olive oil polyphenols. Biochem Biophys Res Commun 247:60-4, 1998.

Visioli F. et al., Oleuropein protects low-density lipoprotein from oxidation. Life Sci 55:1965-71, 1994.

Wada T et al., The therapeutic effect of bovine lactoferrin in the host infected with *Helicobacter pylori*. Scand J Gastroenterol 34:238-43, 1999.

Yamauchi et al., Effects of orally administered bovine lactoferrin on the immune system of healthy volunteers. Adv Exp Med Biol 443:261-5, 1998.

Zimecki M et al., Oral treatment of rats with bovine lactoferrin inhibits carrageenan-induced inflammation: Correlation with decreased cytokine production. Arch Immunol Ther Exp Warsz 46:361-5, 1998.

Zimecki et al., Immunoregulatory effects of a nutritional preparation containing bovine lactoferrin taken orally by healthy individuals. Arch Immunol Ther Exp Warsz 46:231-40, 1998.

Naidu, A.S. et al. Probiotic Spectra of Lactic Acid Bacteria, Criteria Reviews in Food Science and Nutrition, vol. 38, Issue 1, 1999, pp. 13-126.

Naidu AS et al., Comparison Between Lactoferrin and Subepithelial Matrix Protein Binding in *Stapylococcus aureus* Associated with Bovine Mastitis,. J Dairy Sci 74:3353-9, 1991.

Naidu, A.S. et al. Influence of Lactoferrin on Host-Microbe Interactions. In: Lactoferrin: Interactions and Biological Functions, T.W. Hutchens, B. Lonnerdal, eds., Humana Press Inc., Totowa, NJ, pp. 259-275, 1997.

Naidu, A.S. et al. Lactoferrin Interaction with Salmonellae Potentiates Antibiotic Susceptibility in Vitro. Diagn. Microbiol. Infect. Dis., 20:69-75, 1994.

Naidu, A.S. et al. Bovine Lactoferrin Binding to Six Species of Coagulase-Negative *Staphylococci* from Bovine Intramammary Infections. J. Clin. Micro., 28:2312-2319, 1990.

Naidu, A.S. et al. Identification of a Human Lactoferin-Binding Protein in *Staphylococcus aureus*, J. Med. Microbiol., 36:177-183, 1992.

Naidu, A.S. et al. Milk Lactoferrin-Natural Microbial Blocking Agent (MBA) for Food Safety, Environmental & Nutritional Interactions, 2:35-50, 1998.

Naidu, A.S. et al. Reduction of Sulfide, Ammonia Compounds, and Adhesion Properties of *Lactobacillus casei* Strain KE99 in Vitro. Current Microbiology, 44:196-205, 2002.

Naidu, A.S. et al. Probiotics. In: Natural Food Antimicrobial Systems, A.S. Naidu, ed., CRC Press, Boca Raton, pp. 432-462, 2000.

Naidu, S.S. et al. Relationship Between Antibacterial Activity and Porin Binding of Lactoferrin in *Escherichia coli* and *Salmonella typhimurium*. Antimicrobial Agents Chemo., 37:240-245, 1993.

Naidu, S.S. et al. Specific binding of lactoferrin to *Escherichia coli* isolated from human intestinal infections. APMIS, 99:1142-1150, 1991.

* cited by examiner

TREATMENTS FOR CONTAMINANT REDUCTION IN LACTOFERRIN PREPARATIONS AND LACTOFERRIN-CONTAINING COMPOSITIONS

RELATED APPLICATIONS

The present application is a divisional of U.S. patent application Ser. No. 11/072,054, filed Mar. 3, 2005, now U.S. Pat. No. 7,125,963, which claims priority to U.S. Provisional Patent Application No. 60/549,998 filed Mar. 3, 2004.

FIELD OF THE INVENTION

This invention relates to a method of ultra-cleansing preparations of commercially available lactoferrin (LF) to render them suitable for prebiotic as well as other functional in vivo applications. Additionally the invention relates to physiological delivery systems for prebiotic lactoferrin compositions with or without supplementation with probiotic lactic acid bacteria and other bioactive compounds.

BACKGROUND OF THE INVENTION

The emerging knowledge on diseases and the role of natural foods in lowering the risk of such disease process have furthered research efforts for identification and development of nutritionally important dietary supplements. Milk is the first complete delivery system for essential nutrients in the newborn. This natural delivery system provides several bioactive components for critical management of gastrointestinal functions including defense against microorganisms, toxin and free radical scavenging, gut maturation and repair, nutrient diffusion and transport across mucosal barrier and prebiotic activity. Accordingly, the consumption of cow's milk has been an integral part of human civilization since antiquity and this natural delivery system has provided remarkable benefits to mankind.

Lactoferrin (LF) is a major bioactive constituent of milk. This iron-binding protein is responsible for a wide range of nutraceutical benefits and provides protection against several intestinal illnesses. LF plays an important role in various physiological pathways including inflammation by promoting neutrophil aggregation, inhibition of antibody-mediated cytotoxicity, specific growth stimulation of lymphocytes, down-regulation of myelopoiesis, complement cascade modulation by C3 convertase inhibition, intestinal iron absorption, enterocyte proliferation and gut maturation, up-regulation of thymocyte maturation, up-regulation of monocyte cytotoxicity, regulation of antibody production, regulation of cytokine production, down-regulation of tumor necrosis factor (TNF) and prevention of hydroxyradical-mediated tissue injury. Though iron chelation is considered an important molecular property of LF, a number of cellular functions are independent of this metal-binding property of LF. Specific and non-specific interactions of LF with cells, co-existence with a variety of biomolecules in different environments, molecular heterogeneity and structural flexibility confers a spectrum of multifunctionality to the LF molecule in vivo (Naidu A S, Arnold R R, Influence of lactoferrin on host-microbe interactions. In 'Lactoferrin Interactions and Biological Functions, ed. T W Hutchens, B. Lonnerdal, pp. 259-75. Totowa, N. J., Humana Press, 1995; Naidu A S, Bidlack W R, Milk lactoferrin—Natural microbial blocking agent for food safety. Environ Nutr Interact 2:35-50, 1998).

The multifunctional activities of LF documented in several clinical trials and in vivo studies, demonstrate that this milk protein provides an excellent prebiotic physiological delivery system for the gastrointestinal tract.

Lactoferrin has been shown to modulate mucosal immunity. Oral administration of bovine LF (40 mg/day) in healthy human volunteers (n=17) results in an augmentation of their immune responses (Zimecki et al., Immunoregulatory effects of a nutritional preparation containing bovine lactoferrin taken orally by healthy individuals. Arch Immunol Ther Exp Warsz 46:231-40, 1998). Human clinical trials in Japan demonstrated a positive influence of LF consumption in primary activation of host defense. Healthy male volunteers (n=10) fed with bovine LF (2 g/day for a week) showed an improvement in their serum neutrophil function such as enhanced phagocytic activity and superoxide production by neutrophils (Yamauchi et al., Effects of orally administered bovine lactoferrin on the immune system of healthy volunteers. Adv Exp Med Biol 443:261-5, 1998). Furthermore, specific interaction of LF with alveolar macrophages, monocytes, Kupfer cells, liver endothelia, peripheral mononuclear lymphocytes, platelets, and T-lymphocytes emphasizes the role of LF in mucosal and cellular immunity.

Additionally, LF has anti-tumor activity. Activated monocytes are able to kill tumor cells and mediate antibody-dependent cell-mediated cytotoxicity. Lactoferrin markedly affects adherent monocyte toxicity, but has no effect on nonadherent lymphocytes (T-cells). Lactoferrin also enhances the natural killer (NK) activity of cells in a dose-dependent manner and augments both NK and lymphokine-activated killer (LAK) cell cytotoxic functions (Shau et al., Modulation of natural killer and lymphokine-activated killer cell cytotoxicity by lactoferrin. J Leukoc Biol 51:343-9, 1992). Lactoferrin is an effective modulator of cell-mediated immune responses, including serum cytotoxic factors, at low dosages (<1 μg/ml) however, at higher concentrations, LF-mediated induction could lead to positive or negative feedback responses, depending on the numbers and subsets of the immune cell population. Immunomodulator effects of LF, particularly the NK and LAK functions, are iron-independent, since the depletion of iron from LF by the chelator desferoxamine does not affect the cytotoxic augmentation capacity of LF. Discovery of specific LF receptors on macrophages, T- and B-lymphocytes and leukemic cells further establishes the anti-tumor potential of LF.

Lactoferrin is central to intestinal iron absorption. Research on iron absorption from milk LF has received much attention in recent years and has contributed to the development of several infant formulae (Lonnerdal B, Trace element absorption in infants as a foundation to setting upper limits for trace elements in infant formulas. J Nutr Suppl 119:1839-44, 1989). Lactoferrin has been suggested to play an important role in the intestinal absorption of iron, zinc, copper, manganese and other essential trace elements and has also been suggested to protect the gut mucosa from excess uptake of heavy metal ions. Specific LF binding receptors in the human duodenal brush border are involved in iron absorption (Cox et al., Iron-binding proteins and influx of iron across the duodenal brush border. Evidence for specific lactotransferrin receptors in the human small intestine. Biochem Biophys Acta 588:120-8, 1979). An intestinal receptor for LF ($M_r$ 110 kDa) with a cellular density of $4.3 \times 10^{14}$ sites per milligram of solubilized human fetal intestinal brush-border membranes (IBBM) has been isolated (Kawakami H, Lonnerdal B, Isolation and function of a receptor for human lactoferrin in human fetal intestinal brush-border membranes. Am J Physiol 261:G841-6, 1991). Furthermore, increased iron absorption via this LF receptor from IBBM during the neonatal period has been reported (Rosa G, Trugo N M, Iron uptake from lactoferrin by intestinal brush-border membrane vesicles of human neonates. Braz J Med Biol Res 27:1527-31, 1994).

The gastrointestinal tract matures most rapidly in the newborn during the period when the newborn is nursing. Human milk has been shown to stimulate thymidine uptake in a variety of fibroblast cell lines and various substances in human milk, such as epidermal growth factor, have been identified as potent mitogens. Oral administration of LF, either at low (0.05 mg/g body weight per day) or high (1 mg/g body weight per day) dosages functions as an immune stimulating factor on the intestinal mucosa and this activation is dependent on LF binding to the intestinal epithelia (Debbabi H et al., Bovine lactoferrin induces both mucosal and system immune responses in mice. J Dairy Res 65:283-93, 1998). Later studies have demonstrated that LF potentiates thymidine incorporation into rat crypt cell DNA (Nichols B L et al., Iron is not required in the lactoferrin stimulation of thymidine incorporation into the DNA of rat crypt enterocytes. Pediatr Res 27:525-8, 1990). This trophic effect may also contribute to cell regeneration and tissue repair of intestinal mucosa in conditions such as gastroenteritis. Anabolic effects of orally administered bovine LF on visceral organ growth and protein synthesis have been evaluated in an unsuckled newborn piglet model. Animals (n=18) were randomly assigned to one of three dietary treatment groups: i) formula alone (10 mL/h), ii) formula with physiologic levels (1 mg/mL) of bovine LF or iii) formula with colostrum. After 24 h of feeding, hepatic protein synthesis in animals fed either formula containing LF or colostrum was similar and was significantly higher than the formula alone control group. These results indicate that feeding of LF-supplemented formula increases hepatic protein synthesis in the newborn, suggesting an anabolic function for LF in the neonates (Burrin D G et al., Orally administered lactoferrin increases hepatic protein synthesis in formula-fed newborn pigs. Pediatr Res 40:72-6, 1996).

Lactoferrin's interaction with neutrophils and mononuclear phagocytes is potentially of great importance in a variety of inflammatory processes. When given orally (10 mg×5 doses on alternate days), LF inhibits carrageenan-induced inflammation by 40-50%. This inhibition is associated with a substantial decrease in IL-6 production by splenocytes and LPS-induced TNF-α production. The decreased ability of spleen cells to produce inflammatory cytokines in the LF-treated group indicates that hyporeactivity of the immune system cells may be the basis for the inhibition of carrageenan-induced inflammation (Zimecki M et al., Oral treatment of rats with bovine lactoferrin inhibits carrageenan-induced inflammation: Correlation with decreased cytokine production. Arch Immunol Ther Exp Warsz 46:361-5, 1998).

Removal of endotoxins and cholesterol from the GI tract is another function of LF. Bovine LF is protective against lethal shock induced by intravenously administered endotoxin as evaluated in a germ-free, colostrum-deprived, immunologically 'virgin' piglet model. Pre-feeding with LF resulted in a significant decrease in piglet mortality compared to control animals (16.7% mortality in LF-treated animals versus 73.7% mortality in controls) (Lee W J et al., The protective effects of lactoferrin feeding against endotoxin lethal shock in germfree piglets. Infect Immun 66:1421-6, 1998). Lactoferrin-mediated protection against endotoxin challenge was also correlated with both resistance to induction of hypothermia and an overall increase in wellness. In vitro studies using a flow cytometric assay system demonstrated that endotoxin binding to porcine monocytes was inhibited by LF in a dose-dependent fashion, suggesting that the mechanism of LF action in vivo could be possibly due to the prevention of induction of monocyte/macrophage-derived inflammatory-toxic cytokines.

Oral administration of bovine LF with milk suppressed the proliferation of intestinal *clostridium* species and fecal excretion of anaerobic pathogens (Teraguchi S et al., Bacteriostatic effect of orally administered bovine lactoferrin on proliferation of *Clostridium* species in the gut of mice fed bovine milk. Appl Environ Microbiol 61:501-6, 1995). Furthermore, supplementation of milk with bovine LF also suppresses bacterial translocation, mainly members of the family Enterobacteriaceae, from the intestines to the mesenteric lymph nodes (Teraguchi S et al., Orally administered bovine lactoferrin inhibits bacterial translocation in mice fed bovine milk. Appl Environ Microbiol 61:4131-4, 1995). Oral administration of a solution of 1% bovine LF for three to four weeks decreased *Helicobacter pylori* counts in the stomach by 10% and also exerted a potent inhibitory effect on the gut attachment of the bacterium. This resulted in a marked decline in the serum antibody titer against *H. pylori* to an undetectable level (Wada T et al., The therapeutic effect of bovine lactoferrin in the host infected with *Helicobacter pylori*. Scand J Gastroenterol 34:238-43, 1999). Prophylactic and therapeutic effects of oral dosages of LF against intractable stomatitis in vivo have also been reported (Sato N et al., Lactoferrin inhibits *Bacillus cereus* growth and heme analogs recover its growth. Biol Pharm Bull 22:197-9, 1999).

Certain bioactive components of milk have prebiotic activity and promote growth of beneficial bacteria such as *Lactobacillus* spp. and *Bifidobacterium* spp. in vivo. It is known that the large intestine of breast-fed infants is colonized predominantly by *Bifidobacterium* spp., which have protective effects against enteric pathogens. Earlier studies suggested that LF derived from human and bovine sources of mature milk enhances the growth of *B. infantis, B. breve* and *B. bifidum* in vitro, in a dose-dependent manner (Roberts A K et al., Supplementation of an adapted formula with bovine lactoferrin—effects on the infant faecal flora. Acta Paediatr 81:119-24, 1992). Feeding trials with infant formula with LF supplementation (100 mg/mL) established bifidus flora in 50% of the infants at age three months. Certain peptide domains on LF have been identified to stimulate growth of *Bifidobacterium* spp. in vivo (Petschow B W et al., Ability of lactoferrin to promote the growth of *Bifidobacterium* spp. in vitro is independent of receptor binding capacity and iron saturation level. J Med Microbiol 48:541-9, 1999; Liepke C et al., Human milk provides peptides highly stimulating the growth of bifidobacteria. Eur. J. Biochem. 269:712-8, 2002; Lonnerdal B, Nutritional and physiologic significance of human milk proteins. Am J Clin Nutr 77:1537S-153S 2003).

Thus, the combination of prebiotic activity with multifunctional activities described herein makes LF a powerful nutraceutical for regulating the microbial balance, mucosal defense, nutrient absorption and healthy maintenance of the gastrointestinal tract.

Oral administration of LF, and its role as a multifunctional delivery system in the gastrointestinal tract, is clearly established in research laboratories and in several experimental trials worldwide. However, to further any commercial exploitation of LF as a prebiotic system for human health application requires an innovative technology compatible with large-scale manufacturing practices. Such technology transfer must ensure the highest standards of product safety, quality assurance and delivery of an optimal dosage for an effective functional outcome. There are four major issues critical for the commercialization of LF as a prebiotic in vivo delivery system including bioactivity, microbiological quality, endotoxin content and dosage.

First we will address the issue of bioavailability. Like most multifunctional proteins, LF activity is highly dependent on the three-dimensional or tertiary structure of the molecule. Thus, the stability of LF protein could limit its usefulness. Conditions such as the presence of metals (iron, in particular), anionic ions, salts, pH, temperature and conductivity are known to affect the functional properties of LF. Furthermore, protein isolation and processing conditions including storage, freezing/thawing, and spray-drying could also adversely affect LF bioactivity. Degradation of native LF into peptic fragments as well as the co-elution of impurities from raw material could further compromise LF applications. Therefore, LF could denature or inactivate to partially or totally lose its functional properties during large-scale manufacturing.

U.S. Pat. No. 6,172,040 to Naidu teaches certain immobilized forms of LF and their antimicrobial applications. The immobilization method disclosed in the Naidu patent relates to an ex vivo orientation of the LF molecule similar to its molecular configuration when bound to mammalian mucosa, as well as to an increased structural stability of the LF protein and to an optimal neutralization of cationic peptides to eliminate undesirable non-specific bactericidal effects. Furthermore, this immobilization step, in combination with certain formulation conditions, could potentiate LF into a powerful antibiotic that serves as an excellent system to protect against harmful pathogens. However, immobilized lactoferrin is neither designed nor is reported to have prebiotic activity.

The microbiological quality of LF starting raw materials could significantly compromise the human health applications of commercial LF. Several factors including the source of raw starting material, protein separation and harvesting methods, and manufacturing environment and storage conditions all cumulatively contribute to the LF bio-burden. Accordingly, when used as a raw starting material, whey or milk serum has the potential to carry-through fermentative streptococci (*Streptococcus thermophilus*, in particular) and in an acid environment could selectively enrich several yeast and molds. These microbial populations are commonly known to proliferate and competitively limit several strains of probiotic bacteria. Lactoferrin derived directly from the milk source could minimize the above problem, however contamination of the milk pool from cows with bovine mastitis could introduce several Gram-positive cocci such as *Strep. uberis*, *Staphylococcus aureus* and coagulase-negative staphylococci. Additionally, environmental contaminants such as spore-forming *Bacillus* spp., *Acinetobacter calcoaceticus*, *Klebsiella oxytoca*, *Pseudomonas* spp., and coliforms including *Escherichia coli* could gain entry into LF material through elution buffers, biofouled equipment and air ducts. Similarly, microbiological quality issues also exist for genetically modified organism (GMO)-derived and recombinant LFs from various expression sources such as rice, tobacco, yeast, cell cultures or transgenic animals. Therefore, elimination or significant reduction of such microbial contaminants is highly critical for human health applications of commercially available LF and for developing prebiotic delivery systems.

The endotoxin content of LF starting raw material could also adversely affect its human health applications. Lipopolysaccharides (LPS) are the outer membrane components of Gram-negative bacteria that typically consist of hydrophobic domain known as lipid-A (or endotoxin), a non-repeating core oligosaccharide, and a distal polysaccharide (or O-antigen). Endotoxins stimulate the production of cytokines and other mediators of inflammation, which in turn trigger a broad range of adverse physiological responses. Experimental evidence suggests that reactive oxygen species are important mediators of cellular injury during endotoxemia, either as a result of macromolecular damage or by interfering with extracellular and intracellular regulatory processes. In addition, nitric oxide is thought to play a key role in the pathogenesis of endotoxic shock. The Gram-negative bio-burden of milk or its derivatives used in the LF isolation, processing plant environment and conditions cumulatively contribute to the endotoxin levels in LF material. The potential sources of endotoxin contamination during isolation of protein materials have been recently reviewed (Majde J A, Microbial cell-wall contaminants in peptides—a potential source of physiological artifacts. Peptides 14:629-32, 1993). Additionally, Rylander (Rylander R, Endotoxin in the Environment—exposure and effects. J Endotoxin Res 8:241-52, 2002) has reviewed the occurrence of endotoxin in different environmental conditions and further pointed out the risks associated with non-bacterial endotoxins, particularly 1,3-$\beta$-D-glucan from mold cell walls. Thus, the microbiological standards of chromatographic resins, sanitation practices of processing equipment and even more significantly the water quality used in LF isolation, could cumulatively contribute to the endotoxin levels of the isolated LF material and thereby could limit the in vivo applications of commercial LF.

Since LF is a multifunctional protein with a defining role in various physiological pathways, its activity is highly dependant on dosage and a proper delivery system. Regulatory proteins are like traffic signals and thus at optimal dosages function positively in a beneficial manner promoting a physiological function, while at other dosages (usually high concentrations) function negatively through feedback inhibition by blocking body functions. In order to maintain an optimum physiological balance, LF is cleared by liver and spleen at a catabolic rate of 5.7 mg/day (Bennett R M, Kokocinski T, Lactoferrin turnover in man. Clin Sci 57:453-60, 1979).

Lactoferrin co-exists with an array of molecules in different mucosal secretions under varying environmental or physiologic conditions. These substrates and/or physiochemical conditions exert a specific effect on the structural reorganization of LF molecule and thereby define its multifunctional properties. In humans, the normal levels of LF are 1-2 mg/mL in breast milk, tears and gastric mucins, 0.1-1 mg/mL in saliva, crevicular fluids, and sperm, <0.01 mg/mL in synovial fluids and plasma and the secondary granules of neutrophils contain about 0.01 mg/$10^6$ cells. However, these levels significantly rise by 10- to 100-fold during infections such as mastitis and parotitis (Tabak L et al., Changes in lactoferrin and other proteins in a case of recurrent parotitis. J Oral Pathol 1:97-9, 1978; Harmon R J et al., Changes in lactoferrin, immunoglobulin G, bovine serum albumin, and $\alpha$-lactalbumin during acute experimental and natural coliform mastitis in cows. Infect Immun 13:533-42, 1976). In such abnormal conditions, LF aggregates into dimeric and tetrameric complexes that could subsequently lead to LF dysfunctionality. (Bennett R M et al., Calcium-dependant polymerization of lactoferrin. Biochem Biophys Res Commun 101:88-95, 1981).

Lactoferrin dosage, therefore, is highly critical in the development of any in vivo delivery system. Furthermore, in the design of such a therapeutic, estimation of average daily intake (ADI) values for LF in the human plays a significant role. According to the United States Department of Agriculture (USDA) Continuing Survey of Food Intakes by Individuals (CSFII) data from 1994-96, the average intake of milk and milk products on both a gram per day (g/d) and gram per kilogram of body weight per day (g/kg bw/d) have been calculated. The CSFII 1994-96 data is based on dietary information from individuals of all ages collected between January 1994 and January 1997. Considering that cow's milk contains 0.1 mg/mL to 0.2 mg/mL of LF, on an average, children 1 to 12 years old and teens 13 to 19 years old consume about 396 g milk/day and 377 g milk/day, respectively. This is equivalent to 38 to 40 mg LF/day. Adults (20+) consume less milk, 240 g/d and their intake of LF is equal to about 24 mg/day. The consumption of LF for milk consumers in the $90^{th}$ percentile averages 73 mg/d for children, 75 mg/d for teens and 50 mg/d for adults.

SUMMARY OF THE INVENTION

The present invention provides a method of treatment for contaminant reduction (TCR) that ultra-cleanses commercial freely-dispersed native lactoferrin [(fdn)-LF] preparations from contaminant activity, leading to significant reductions and/or elimination of viable microbial load and endotoxin activity. The TCR method of the present invention renders these (fdn)-LF preparations suitable for prebiotic in vivo applications, particularly as physiologic delivery systems to enhance health benefits in the host with or without supplementation of probiotic lactic acid bacteria (LAB). Additionally the present invention provides for compositions which contain LF-TCR and optionally surfactants, antioxidants, polyphenols and anionic compounds. The therapeutic lactoferrin composition can additionally contain bioactive agents, dietary supplements, nutraceuticals/functional foods, tissue/membrane diffusion facilitating agents, prophylactic agents, therapeutic agents and probiotic lactic acid bacteria.

In an embodiment of the present invention, a method of preparing an ultra-cleansed lactoferrin preparation, termed treatment for contaminant reduction (TCR) is provided comprising the steps of treating a commercial lactoferrin preparation with at least one surfactant, contacting the surfactant-treated lactoferrin with at least one antioxidant, purifying the antioxidant-treated lactoferrin with at least one polyphenol, removing endotoxin from the polyphenol-treated lactoferrin to form purified lactoferrin (LF-TCR), and drying the LF-TCR.

In an embodiment of the present invention, ultra-cleansed lactoferrin preparation is purified from commercially available lactoferrin isolated from dairy sources including colostrum, milk, whey and milk serum from humans, cows, buffalos, horses, sheep, pigs or camels. Additionally the ultra-cleansed lactoferrin preparation can be purified from recombinant sources and genetically-modified organisms (GMOs).

In another embodiment of the present invention, the TCR method utilizes surfactants including food-grade detergents, bile salts and plant saponins. Food grade detergents useful in the present invention include polysorbate-20, polysorbate-40, polysorbate-60, and polysorbate-80. Bile salts useful in the present invention include bile salts isolated from pigs and cows. Plant saponins useful in the present invention include extracts from plants such as quillaya, yucca, soy, green tea, ginseng and fenugreek. In an embodiment of the present invention, the concentration of surfactant is approximately 0.01 mg to 1,000.00 mg for each 100 mg of lactoferrin, and optionally approximately 1.00 mg to 10.00 mg for each 100 mg lactoferrin.

In yet another embodiment of the present invention, the TCR method utilizes antioxidants including Vitamin A, Vitamin C, Vitamin E and metal chelators such as citrate, citrate derivatives, trisodium phosphate and ethylenediaminetetraacetic acid. In an embodiment of the present invention, the concentration of antioxidant is approximately 0.01 mg to 10,000.00 mg for each 100 mg of lactoferrin, and optionally approximately 1.00 mg to 100.00 mg for each 100 mg lactoferrin.

In an embodiment of the present invention, the TCR method utilizes polyphenols including oleoresins, aquaresins, terpenes, flavonoids and biliproteins. Oleoresins useful in the present invention include curcumin, curcuminoids, thymol, borneol, catechol, and olive-extracted oleuropein. Aquaresins useful in the present invention include extracts of turmeric, ginger, clove and cinnamon. Terpenes useful in the present invention include carvacrol, 6-gingerol, piperine, camphor, camphene, α-pinene, quercetin and tree-tea oil. Flavonoids useful in the present invention include chalcones, dihydroflavones (flavanone), flavones, biflavonoids, dihydroflavonols, flavonols, anthocynidins and proanthocyanidin tannins. Biliproteins useful in the present invention include phycocyanins from blue-green algae or phycocyanobilins from a *Spirulina* species. In an embodiment of the present invention, the concentration of polyphenol is approximately 0.01 mg to 10,000.00 mg for each 100 mg of lactoferrin, and optionally approximately 1.00 mg to 100.00 mg for each 100 mg lactoferrin.

In another embodiment of the present invention, the TCR method further includes an anionic compound in the antioxidant step. Anionic compounds useful in the present invention include carbonates, bicarbonates or carbonated liquids.

In an embodiment of the present invention, a therapeutic lactoferrin composition is provided comprising LF-TCR, at least one surfactant, at least one antioxidant, at least one polyphenol and at least one anionic compound.

In another embodiment of the therapeutic lactoferrin composition of the present invention, the surfactant includes food-grade detergents, bile salts and plant saponins.

In yet another embodiment of the therapeutic lactoferrin composition of the present invention, the antioxidant includes Vitamin A, Vitamin C, Vitamin E and metal chelators.

In an embodiment of the therapeutic lactoferrin composition of the present invention, the polyphenol includes oleoresins, aquaresins, terpenes, flavonoids and biliproteins.

In another embodiment of the therapeutic lactoferrin composition of the present invention, the anionic compound includes carbonates, bicarbonates or carbonated liquids.

In yet another embodiment of the therapeutic lactoferrin composition of the present invention, the therapeutic lactoferrin further contains at least one additional agent selected from the group including bioactive agents, dietary supplements, nutraceuticals/functional foods, tissue/membrane diffusion facilitating agents, prophylactic agents and therapeutic agents. Bioactive agents useful in the therapeutic lactoferrin composition of the present invention include immunoglobulins, lactoperoxidase, glycomacropeptide, conalbumin (ovotransferrin), lysozyme and avidin. Dietary supplements useful in the therapeutic lactoferrin composition of the present invention include vitamins, folic acid, biotin, enzymes, co-enzymes, amino acids, grape seed and skin extracts, cranberry extracts and minerals. Nutraceuticals/functional foods useful in the therapeutic lactoferrin composition of the present invention include soy proteins, flaxseed oil, lycopenes, allicin/ajoene, catechins, omega fatty acids, yoghurt and fermented dairy products. Tissue/membrane diffusion facilitating agents useful in the therapeutic lactoferrin composition of the present invention include dimethylsulfoxide, petrolatum and sodium lauryl sulfate. Prophylactic agents useful in the therapeutic lactoferrin composition of the present invention include vaccines, immune boosters and probiotic agents. Therapeutic agent useful in the therapeutic lactoferrin composition of the present invention include antibacterial agents, antifungal agents, antiviral agents and antiparasitic agents.

In an embodiment of the present invention, the daily dose of lactoferrin is approximately 0.01 to 10,000 mg per day, optionally approximately 1.0 to 250 mg per day.

In another embodiment of the present invention, the therapeutic lactoferrin composition further contains probiotic lactic acid bacteria including *Lactobacillus* spp., *Leuconostoc* spp., *Bifidobacterium* spp., *Pediococcus* spp., *Peptostreptococcus* spp., *Propionibacterium* spp. and *Streptococcus* spp. *Lactobacillus* species useful in the therapeutic lactoferrin composition of the present invention include *L. acidophilus, L. amylovorus, L. animalis, L. bavaricus, L. brevis, L. bulgaricus, L. casei* ssp *casei, L. casei* ssp *rhamnosus, L. crispatus, L. delbrueckii* ssp *lactis, L. eichmanni, L. fermentum, L. helveticus, L. jensenii, L. kefir, L. paracasei, L. pentosus, L. plantarum, L. reuteri, L. salivarius* and *L. sake*. *Leuconostoc* species useful in the therapeutic lactoferrin composition of the present invention include *Leu. cremoris* or *Leu. lactis*. *Bifidobacterium* species useful in the therapeutic lactoferrin composition of the present invention include *B. adolescentis, B. animalis, B. bifidum, B. breve, B. infantis, B. Iongum* and *B. thermophilum*. *Pediococcus* species useful in the therapeutic lactoferrin composition of the present invention include *Ped. acidilactici* and *Ped. pentosus*. *Peptostreptococcus* species useful in the therapeutic lactoferrin composition of the present invention include *Pep. assacharolyticus* and *Pep. productus*. *Propionibacterium* useful in the therapeutic lactoferrin composition of the present invention include *Pro. acidipropionici, Pro. freudenreichii, Pro. jensenii* and *Pro. theonii*. *Streptococcus* species useful in the therapeutic lactoferrin composition of the present invention include *Strep. cremoris, Strep. faecium, Strep. lactis, Strep. raffinolactis* and *Strep. thermophilus*.

In yet another embodiment of the present invention, the probiotic lactic acid bacteria is in the form of a freeze-dried powder or an emulsion. The probiotic lactic acid bacteria can be a viable bacteria cell preparation or a non-viable bacteria cell preparation. The dose of viable probiotic lactic acid bacteria is in the range of approximately $10^2$ to $10^{12}$ colony forming units per daily dosage of 100 mg lactoferrin. The dose of non-viable probiotic lactic acid bacteria is in the range of approximately $10^2$ to $10^{12}$ bacterial cells per daily dosage of 100 mg lactoferrin.

In an embodiment of the present invention, the therapeutic lactoferrin composition is delivered to a tissue/mucosal site of a recipient in need thereof. The tissue/mucosal site can be the gastrointestinal tract, the oropharyngeal region, the nasopharyngeal region, the vulvo-vaginal region and the skin.

In another embodiment of the present invention, the therapeutic lactoferrin composition is a pharmaceutical formulation such as tablets, capsules, powders, drinks, chewable tablets, mouthwashes, suppositories, douches, ointments, skin cleansing solutions, crèmes, makeup, antiperspirants and shampoos.

In an embodiment of the present invention, the therapeutic lactoferrin composition comprises LF-TCR. In another embodiment of the present invention, the therapeutic lactoferrin composition includes at least one probiotic lactic acid bacteria selected from the group consisting of *Lactobacillus* spp., *Leuconostoc* spp., *Bifidobacterium* spp., *Pediococcus* spp., *Peptostreptococcus* spp., *Propionibacterium* spp. and *Streptococcus* spp. In yet another embodiment of the present invention, the therapeutic lactoferrin composition also optionally includes other agents such as surfactants, antioxidants, polyphenols, anionic compounds, bioactive agents, dietary supplements, nutraceuticals/functional foods, prophylactic agents and therapeutic agents.

DEFINITION OF TERMS

Figure 1:
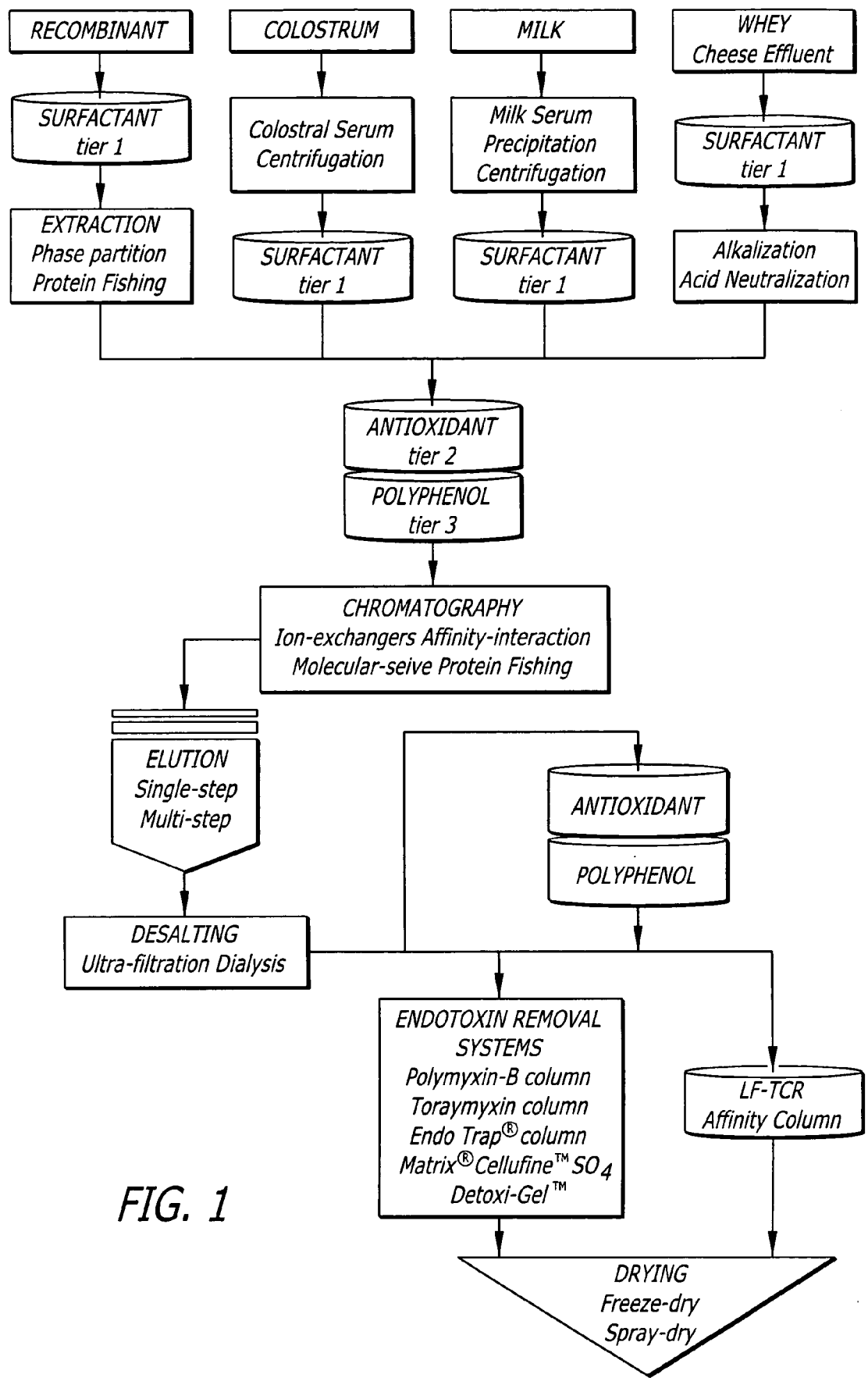
FIG. 1 depicts a flow chart for isolation and purification of LF using the treatment for contamination reduction according to the teachings of the present invention.

Freely-dispersed native lactoferrin: As used herein, "freely-dispersed native lactoferrin" refers to isolated LF protein molecules free of autoaggregation or polymerization and free from binding or immobilization to other substrates.

Lactoferrin: As used herein, "lactoferrin" or "LF" refers to freely-dispersed native (fdn)-lactoferrin which includes metal-saturated (holo), partially saturated and metal-free (apo) forms of LF. The LF-bound metal is preferably iron, and other bound metals include zinc, copper, manganese. The term LF further refers to fully and partially glycosylated polypeptide chains of LF, incomplete polypetide chains including half-molecules comprising C- and N-terminus lobes of LF. The term LF categorically does not refer to aggregated-LF and immobilized (Im)-LF forms that are devoid of any (fdn)-LF.

Prebiotic: As used herein, "prebiotic" refers to compounds, including but not limited to lactoferrin, indigestible carbohydrates and other non-digestible food ingredients, that stimulate the growth and activity of beneficial bacteria already established in the intestines.

Probiotic: As used herein, "probiotic" refers to nutritional supplements of beneficial intestinal bacteria intended to re-colonize the intestines to promote digestive health. A probiotic is also described as a preparation or a product containing viable, defined microorganisms with or without other substances in sufficient numbers, which improve or alter the microflora or their properties (by implantation or colonization) in a compartment of the host and thereby exert beneficial health effects in the host.

Synbiotic: As used herein, "synbiotic" refers to a product which contains both probiotics and prebiotics. Synbiotic products are those in which the prebiotic compound selectively favors the probiotic organism.

DETAILED DESCRIPTION OF THE INVENTION

The present invention provides a method of treatment for contaminant reduction (TCR) that ultra-cleanses commercial freely-dispersed native lactoferrin [(fdn)-LF] preparations from contaminant activity, leading to significant reductions and/or elimination of viable microbial load and endotoxin activity. The TCR method of the present invention renders these (fdn)-LF preparations suitable for prebiotic in vivo applications, particularly as physiologic delivery systems to enhance health benefits in the host with or without supplementation of probiotic lactic acid bacteria (LAB). Additionally the present invention provides for compositions which contain LF-TCR and optionally surfactants, antioxidants, polyphenols and anionic compounds. The therapeutic lactoferrin composition can additionally contain bioactive agents, dietary supplements, nutraceuticals/functional foods, tissue/membrane diffusion facilitating agents, prophylactic agents, therapeutic agents and probiotic lactic acid bacteria.

The present invention therefore provides methods to select and utilize mixtures of natural and/or food-grade substances with free dispersions of LF in order to exert potent selective prebiotic activity, to maximize probiotic benefits of LAB and to create an environment to optimize such activity of LF.

Ultra-cleansed LF preparations made according to the teachings of the present invention are useful as physiologic transport systems to deliver therapeutic and prophylactic agents to mammalian mucosal sites such as the gastrointestinal tract, the oropharyngeal region, the nasopharyngeal region, the vulvo-vaginal region and skin.

Lactoferrin used in accordance with the teachings of the present invention includes LF derived from different sources including lactating mammals, transgenic animals, and genetically-modified organisms (GMOs); mammalian secretions, preferably milk derived from animals including, but not limited to, humans, cows, buffalos, horses, camels, sheep and pigs; milk at any stage of lactation including, but not limited to, colostrum, transitional milk, mature milk or milk in later lactation; derivatives of milk secretions including whey, skim milk and milk serum. The LF is isolated by any conventional protein separation process such as ultra-filtration, aqueous phase-partition and chromatography using ion-exchange, affinity and/or molecular-sieve columns. Suitable bovine LF is also commercially available in the United States from companies including, but not limited to, Glanbia, Wisconsin; Davisco, Minneapolis and Proliant, Iowa; in Europe from Bio-Pole, Belgium and DMV International, The Netherlands; and in Asia and the Far East from Morinaga Milk Company, Japan and Tatua Nutritionals, New Zealand.

Recombinant human LF cloned and expressed by prokaryotic or eukaryotic expression systems is also suitable for use in embodiments of the present invention and are available in United States from companies including, but not limited to, Agennix, Texas; Ventria Bioscience, California and Ferro Dynamics, Texas; and in Europe from Meristem, France and Gene Pharming Europe, The Netherlands.

One embodiment of the present invention is to exploit the prebiotic activity of LF by a mechanism opposite to its antibiotic activity, i.e. LF-mediated iron-deprivation stasis. Accordingly, the core objective of this technology is specific proliferation of probiotic LAB in the gastrointestinal tract and other host compartments. Because of their cytochrome-independent bio-energetic pathways, LAB are iron-independent microflora, therefore iron limitation created by iron-chelators such as LF do not interfere with their viability (Klander O, Weiss N, Regular, nonsporing Gram-positive rods. In 'Bergey's Manual of Systematic Bacteriology', ed. Sneath PHA et al., pp. 1208-34. Baltimore, Williams and Wilkins, 1986; Griffiths E A et al., In vitro growth responses of bifidobacteria and enteropathogens to bovine and human lactoferrin. Dig Dis Sci 48:1324-32, 2003). Furthermore, LF could enhance the proliferation of LAB and thereby could potentiate their probiotic activity (Miller-Catchpole R et al., Lactoferrin can supply iron for the growth of *Bifidobacterium breve*. Natr Res 17:205-13, 1997; Petschow B W et al., Ability of lactoferrin to promote the growth of *Bifidobacterium* spp. in vitro is independant of receptor binding capacity and iron-saturation levels. J Med Microbiol 48:541-9, 1999). Thus, LF is a natural prebiotic for the probiotic LAB resident on mammalian mucosal surfaces. Despite the existing knowledge about the structure, function and properties of LF, effective methods to use LF as a potential prebiotic delivery system have thusfar not been established.

The term probiotic, meaning "for life," is derived from the Greek language. It was first used by Lilly and Stillwell in 1965 to describe substances secreted by one microorganism which stimulates the growth of another" and thus was contrasted with the term "antibiotic. Probiotics are microbial-based dietary adjuvants that beneficially affect the host physiology by modulating mucosal and systemic immunity as well as improving nutritional and microbial balance in the intestinal tract. The term can also be applied to tissue extracts that stimulate microbial growth and can refer to organisms and substances which contribute to intestinal microbial balance or a live microbial feed supplement which beneficially affects the host animal by improving its intestinal microbial balance (Naidu A S, Bidlack W R, Clemens R A, Probiotic spectra of lactic acid bacteria (LAB). Crit. Rev. Food Sci. Nutr. 39: 3-126, 1999).

The term prebiotic was introduced by Gibson and Roberfroid by interchanging the prefix 'pro' in probiotic for 'pre', which means 'before', and defined prebiotics as non-digestible food ingredients that beneficially affect the host by selectively stimulating the growth and/or activity of one or a limited number of bacterial species already established in the colon (Gibson G R, Roberfroid M B, Dietary modulation of the human colonic microbiota—introducing the concept of prebiotics. J Nutr 125:1401-12, 1995). Accordingly, ingestion of probiotics could significantly modulate the colonic microflora, in particular, the probiotic LAB. In accordance with the teachings of the present invention, prebiotics may be consumed either to deliver a viable probiotic or to stimulate the growth of probiotic flora preexisting in a particular host compartment such as the intestinal tract, oral cavity or vaginal mucosa.

The probiotic organisms suitable for use according to the teachings of the present invention include, a physiologically effective dosage of at least one LAB strain, including, but not limited to, strains of bacteria of the genus *Lactobacillus* including *L. acidophilus, L. amylovorus, L. animalis, L. bavaricus, L. brevis, L. bulgaricus, L. casei* spp *casei, L. casei* spp *rhamnosus, L. crispatus, L. delbrueckii* ssp *lactis, L. eichmanni, L. fermentum, L. helveticus, L. jensenii, L. kefir, L. paracasei, L. pentosus, L. plantarum, L. reuteri, L. salivarius*, and *L. sake*; strains of bacteria of the genus *Leuconostoc* including *Leu. cremoris* and *Leu. lactis*; strains of bacteria of the genus *Bifidobacterium* including *B. ado-*

*lescentis, B. animalis, B. bifidum, B. breve, B. infantis, B. longum*, and *B. thermophilum*; strains of bacteria of the genus *Pediococcus* including *Ped. Acidilactici* and *Ped. pentosus*; strains of bacteria of the genus *Peptostreptococcus* including *Pep. assacharolyticus*, and *Pep. productus*; strains of bacteria of the genus *Propionibacterium* including *Pro. acidipropionici, Pro. freudenreichii, Pro. jensenii*, and *Pro. Theonii* and strains of bacteria of the genus *Streptococcus* including *Strep. cremoris, Strep. faecium, Strep. lactis, Strep. raffinolactis*, and *Strep. thermophilus*. The probiotic organisms listed above are collectively known as lactic acid bacteria or LAB.

Lactic acid bacteria are indigenous probiotic microflora of mammalian gastrointestinal tract that play an important role in the host microecology and have been credited with an impressive list of therapeutic and prophylactic effects (Naidu A S, Clemens R A, Probiotics, p. 431-62. In A. S. Naidu (ed), Natural Food Antimicrobial Systems. CRC Press Boca Raton Fla., 2000). These effects include, but are not limited to, maintenance of microbial ecology of the gut, as well as several physiological effects including immunomodulation and pathogen exclusion (Gibson G R et al., Probiotics and intestinal infections p. 10-39, In R. Fuller (ed), Probiotics 2: Applications and practical aspects. Chapman & Hall, London, UK, 1997). Other LAB associated attributes include enzyme release into the intestinal lumen that act synergistically with LAB adhesion to alleviate symptoms of intestinal malabsorption. Furthermore the LAB-released enzymes help regulate intestinal pH that results in increased aromatic amino acid degradation. LAB have also demonstrated the ability to significantly reduce sulfide and ammonia containing compounds in feces and thus reduce the odor and toxicity associated with animal excrements. (Mitsuoka T, Taxonomy & ecology of bifidobacteria. Bifidobacteria Microflora 3:11, 1984; Naidu A S et al., Reduction of sulfide, ammonia compounds and adhesion properties of *Lactobacillus casei* strain KE99 in vitro. Curr. Microbiol. 44:196-205, 2002).

However, the greatest potential for LAB to improve life quality for humans and domestic animals lies in their in vivo probiotic applications. In order for LAB to exhibit beneficial probiotic effects in vivo, the organism must be administered such that it survives for extended time periods in the gut. Therefore it is critical that probiotic LAB strains be selected that possess qualities that prevent their rapid removal by gut contraction. Effective probiotic bacteria should be able to survive gastric conditions and colonize the intestine at least temporarily by adhering to the intestinal epithelium (Havenaar R et al., Selection of strains for probiotic use, p. 209-224. In R. Fuller (ed), Probiotics the scientific basis. Chapman & Hall, London, UK, 1992; Conway P, Selection criteria for probiotic microorganisms. Asia Pacific J Clin Nutr 5:10-14, 1996).

Factors that could limit the commercial exploitation of LF as a prebiotic delivery system are possible denaturation, iron-saturation, and conformational alterations of the LF molecule during the protein purification process, particularly equilibration (pH), elution (ionic) and drying (temperature) conditions. Since LF is a hydrophobic basic protein (pI=7.5-9.5), certain co-eluants and/or impurities, if present during purification, could cause LF aggregation leading to molecular dysfunction.

U.S. Pat. No. 6,172,040 to Naidu teaches an immobilization method to effectively overcome the above limitations and to reverse such dysfunctional forms of LF by using different substrates, particularly a galactose-rich polysaccharide from agar and agar-related compounds. This ex vivo immobilization involves the N-terminal domain of the LF molecule which mimics the in vivo immobilization of the LF molecule. In vivo, LF binds to specific mucosal target sites, particularly heparin sulfate which is also a galactose-rich polysaccharide, in the gastrointestinal tract. This in vivo interaction is important for several physiological pathways including metal absorption, free radical scavenging and tissue protection and antibiotic activity. This immobilization of LF results in enhanced antibiotic activity which is different from in vivo prebiotic applications.

The three-dimensional protein structure and conformation are highly critical for the multi-functional bioactivity of LF. Open (apo-) and closed (holo-) conformational changes are related to the binding of LF to ferric ion in the presence of a carbonate or bicarbonate anion. The N- and C-terminal halves of LF form two separate globular lobes, connected by a short $\alpha$-helix, and carry one iron-binding site each. Each lobe is subdivided into two dissimilar $\alpha/\beta$ domains, one based on a six-stranded mixed $\beta$-sheet and the other on a five-stranded mixed $\beta$-sheet, with the iron site in the inter-domain cleft. The two iron sites appear identical. Each iron atom is coordinated to four protein ligands, two tyrosines, one aspartate and one histidine, and the specific carbonate anion which appears to bind to iron in a bidentate mode. The anion occupies a pocket between the iron and two positively charged groups on the protein, an arginine side-chain and the N-terminus of helix 5, and may serve to neutralize this positive charge prior to iron binding. A large internal cavity, beyond the arginine side-chain, may account for the binding of larger anions as substitutes for carbonate. Residues on the other side of the iron site, near the inter-domain crossover strands could provide secondary anion binding sites and may explain the acid-stability of iron binding by LF in the intestinal tract (Anderson B F et al., Structure of human lactoferrin at 3.2 Å resolution. Proc Natl Acad Sci USA 84:1769-73, 1987; Anderson B F et al., Structure of human lactoferrin—crystallographic structure analysis and refinement at 2.8 Å resolution. J Mol Biol 209:711-34, 1989).

Accordingly, the present invention utilizes carbonate or bicarbonate anions at specific ratios in combination with natural antioxidants including, but not limited to, Vitamin A, Vitamin C, Vitamin E and metal chelators to enhance the anion-dependent LF bioactivity. For the purpose of restoring the anion-dependant bioactivity of commercial LF, methods related to generating carbonated aqueous systems or anaerobic encapsulations are also suitable.

In an embodiment, the method of the present invention, the creation of an anion-rich environment is provided in a biological compartment of a host by introducing a carbonate or bicarbonate compound such as sodium bicarbonate, carbonated liquids such as seltzers, and/or anaerobic microencapsulations, thus inducing LF into a more bioactive form.

Another important factor that could limit the commercial exploitation of LF for prebiotic applications in the gastrointestinal tract is the fact that it contains different microbial contaminants, which are either selectively enriched from the raw source of LF and sustained through the protein isolation procedures or gain entry into the LF final product from the processing environment. Microbial and endotoxin contaminants are common among commercial-scale protein purification processes. Certificates of analysis for commercial LF from bulk suppliers reflect the prevalence of microbial contaminants, which microbial contaminants depended upon the raw source of LF and the protein purification process. The health status of the source dairy animals, cleanliness of the chromatographic columns and material handling practices during the protein purification process all contribute to the bioburden of the final LF product. Current LF protein purification processes do not incorporate any specific antimicrobial and/or detoxification agents or systems to minimize or eliminate microbial contaminants and endotoxins. Therefore, embodiments of the present invention are directed to the ultra-cleansing of commercial LF preparations of microbial contamination by a treatment for contaminant reduction (TCR).

Gram-positive *Bacillus* spp. such as *Bacillus cereus, Bacillus subtilis* and *Bacillus stearothermophilus* are soil- and milk-borne organisms that prevail in adverse conditions by sporulation. Gram-positive *Staphylococcus* spp. such as *Staph. aureus, Staph. epidermidis, Staph.* chromogenes, and *Staph. hyicus* are prevalent in the farm environment and thus are common milk-borne bacteria. These species are also known to be the etiological agents of bovine mastitis. Certain staphylococci evade LF-mediated inhibition by cellular encapsulation. Gram-positive *Streptococcus* spp., such as *Strep. thermophilus* and *Strep. cremoris* are probiotic LAB used as starter cultures in the manufacturing of cheese and several fermented dairy products and thus are common flora in whey-derived LF. On the other hand, *Strep. uberis* is a persistent bacteria which colonizes the bovine udder and a causative agent of mastitis (Naidu A S et al., Comparison between bovine lactoferrin and other protein binding to *Staphylococcus aureus* associated with bovine mastitis. J Dairy Sci 74:3353-9, 1991). Furthermore, several Lancefield Groups of streptococci, including Group-B and Group-D, the common bovine flora, are known to survive pasteurization and other dairy processing conditions. Streptococci derive cellular energy via cytochrome-independent pathways and therefore are not affected by LF-mediated iron-deprivation stasis. Soil inhabitants such as *Acinetobacter calcoaceticus* are multi-drug resistant cocci that frequently contaminate milk and several dairy products (Axelsson L, Lactic acid bacteria—classification and physiology. In 'Lactic acid bacteria—microbiology and functional aspects', ed. S Salminen, pp. 1-72. New York: Marcel Dekker, 1998). The Gram-positive organisms described herein are known to survive extreme processing conditions such as pH, temperature, salts and could be the major contributors to the bioburden of commercial LF material. Such bioburden could significantly compromise the prebiotic application of commercial LF, since these contaminating microflora could proliferate faster than the intended probiotic LAB and/or inhibit the revival and establishment of the essential probiotic LAB resident in the gut by competitive exclusion (Naidu A S et al., Bovine lactoferrin binding to six species of coagulase-negative staphylococci isolated from bovine intramammary infections. J Clin Microbiol 28:2312-9, 1991).

Gram-negative bacteria such as *E. coli, Enterobacter* sp., *Klebsiella* sp., *Citrobacter* sp. and *Pseudomonas* sp. are normal bovine enteric flora as well as commonly occurring coliforms in the water supply. Coliforms may gain entry into milk, whey or processing environment as dairy- or water-borne contaminants. Stress responses combined with bacterial synthesis of acid-shock and/or heat-shock proteins could effectively shield these organisms from the adverse conditions used during the LF purification process. Though most members of the family Enterobacteriaceae are susceptible to the antimicrobial activities of LF, certain species could evade this potent antimicrobial by producing low molecular weight iron-chelators known as siderophores (Crosa J H, Genetics and molecular biology of siderophore-mediated iron transport in bacteria. Microbiol. Rev. 53:517-30, 1989). Thus, the possible extent of coliform counts in a commercial LF preparation could range from a minimal to an absolute zero. The presence of minimal coliform numbers in LF preparations is not a microbiological issue for ex vivo or surface applications. For in vivo prebiotic delivery applications, however, any occurrence of these bacteria could generate an undesirable competition with the essential probiotic LAB intended for a specific health benefit (Storz G, Hengge-Aronis R, Bacterial stress responses. Washington D.C.: ASM Press, 2000).

Furthermore, certain spore-forming molds such as *Aspergillus* spp., *Pencillium* sp. and yeast such as *Rhodospirullum* spp. and *Candida* spp. could contaminate the LF material and thereby contribute to the viable yeast and mold counts of the commercial protein product. Such contamination could be relatively high in GMO-derived LF preparations such as from transgenic plants compared to mammalian-based LF extractions. Furthermore, a yeast-based (*Aspergillus* sp.) fermentation process has also been described for isolation of a certain recombinant LF proteins (U.S. Pat. No. 6,080,559). These contaminants are generally negligible and present little risk for ex vivo and/or surface applications of commercial LF. However, for in vivo prebiotic supplement applications, the presence of yeast and mold in LF could severely interfere with the probiotic functionality of the LAB as well as be a health hazard.

The present invention discloses a method for preparing a composition to reduce microbial contamination problems associated with commercial LF. Accordingly, this method consists of a multi-tier approach to contaminant exclusion that facilitates an effective in vivo use of commercial LF preparations for prebiotic oral administration purposes.

FIG. 1 provides a flow chart of the LF isolation and purification process using TCR according to the teachings of the present invention. Lactoferrin from a variety of sources including, but not limited to, recombinant LF, colostrum, milk and whey, is first subjected to surfactant treatment (tier one) in order to disrupt contaminant cell membranes. Colostrum and milk sources of LF first undergo a centrifugation or precipitation step before surfactant treatment. The recombinant-derived LF undergoes extraction including phase partitioning and/or protein fishing after surfactant treatment. The whey-derived LF also has a post-surfactant first tier step of acid neutralization.

After a selective surfactant treatment (tier one), LF from all sources is subjected to similar decontamination treatment processes. The decontamination steps consist of an antioxidant/metal chelation treatment (tier two) and a polyphenol treatment (tier three) prior to the chromatographic separation, elution and desalting of the LF. An additional round of antioxidant and polyphenol treatment is optionally incorporated along with endotoxin removal using commercial kits or passage over an LF affinity column. The purified LF-TCR is then dried by a method including, but not limited to, spray-drying or freeze drying. The purified LF-TCR is then ready for use as a prebiotic or as a physiologic delivery system according to the teachings of the present invention.

In an embodiment of the present invention, a method is provided which includes the creation of a surfactant system analogous to physiological gastric detergents to selectively disrupt the cell membranes of any contaminant microflora. Natural and/or food-grade surfactants suitable for use in the present invention include, but not limited to, plant-derived saponins such as extracts from *quillaya* (*Quillaya saponaria*), *yucca* (*Yucca schidigera*), soy (*Glycine max*), green tea (*Camelia sinensis*), *ginseng* (*Panax ginseng*), and *fenugreek* (*Trigonella faenum-graecum*), food-grade polysorbates including, but not limited to, polysorbate-20, polysorbate40, polysorbate-60 and polysorbate-80, and animal-derived bile salts from bovine and porcine gut in sufficient amounts to prevent proliferation of microbial contaminants either alone or in combination.

Surfactants with direct antimicrobial activity can disrupt and/or lyse LF-borne microbial contaminants. Furthermore, these surfactants alter the membrane permeability of microbial cells by a detergent polarization effect and thereby could synergistically potentiate other antimicrobial systems including LF. Thus, any contaminants that possibly evade the first tier exclusion by surfactants, consequently encounter a synergistic inhibitory activity at the second tier by LF itself. In the case of probiotic LAB, however, this indigenous flora is resistant to physiological surfactants such as bile salts in the gastric lumen which is the basic mechanism of their survival in the intestinal tract. Thus, both tiers one and two of the TCR system of the present invention selectively exclude the probiotic LAB from their cytotoxic actions with no detrimental effects whatsoever on their viability and proliferation.

In another embodiment of the present invention, a second tier treatment containing an antioxidant/metal chelation step is included. Antioxidants suitable for use in the second tier of the method of the present invention include, but are not limited to, Vitamins A, C and E. Additional compounds with potential to be useful as antioxidants are the phytochemicals discussed below. Metal chelators useful in the second tier of the method of the present invention include, but are not limited to ethylenediaminetetraacetic acid (EDTA), trisodium phosphate and derivatives of citric acid.

An embodiment of the present invention further teaches the use of effective and permissible amounts of food-grade phytochemicals (polyphenols) to neutralize endotoxin contaminants in commercial LF preparations in the third tier of the method of the present invention. Polyphenols of particular use for this purpose include, but are not limited to, oleoresins (eg. curcumin, borneol and thymol), aquaresins (eg. extracts of turmeric, ginger, clove and cinnamon), oleuropeins (eg. virgin olive extracts), terpenes (eg. piperine, camphor, carvacrol, 6-gingerol and tree-tea oil), flavonoids (eg. extracts of cranberry, grape skin and green tea) and biliproteins (eg. phycocyanins such as *spirulina*). For the purposes of this application turmeric, turmeric root extract and curcurmin are synonymous.

Gram-negative bacteria contain endotoxin (lipid A moiety of lipopolysaccharides) which is released from their outer membrane by bacterial decay (Erridge C et al., Structure and function of lipopolysaccharides. Microbes Infect 4:837-51, 2002). Endotoxins play an important role in the pathogenesis of Gram-negative bacterial sepsis and septic shock, which could result in morbidity and death. Endotoxin interacts with inflammatory cells and release endogenous mediators such as cytokines, hydrolases, peptides, prostaglandins and other compounds that contribute to the pathophysiology of septic shock (Raetz C R, Whitfield C, Lipopolysaccharide endotoxins. Annu Rev Biochem 71:635-700, 2002). Endotoxin enters into the circulatory system via Gram-negative bacteremia and/or translocation of bacteria and bacterial products from the gut. Endotoxin may also enter the circulation as the result of accidental injection of contaminated fluids or through release of endotoxin from bacteria lysed as a consequence of antibiotic therapy.

There is a physiological transfer of endotoxin from the intestine into the blood even in healthy persons. Elimination of endotoxin from portal vein blood occurs primarily in the liver. To protect organs from damage, plasma in healthy persons can inactivate the endotoxin that is continually transferred from the intestine, although this mechanism has not yet been explained. Intestinal permeability disturbances may result in increased transfer of endotoxin from the intestine into the bloodstream. Such disturbances occur, for example, following disruption of microcirculation due to shock or inflammatory intestinal diseases or under immunosuppressive therapy. Increased endotoxin transfer from the intestine into the blood is also observed following enteral antibiotic therapy leading to increased endotoxin release in the intestine. Release of large amounts of endotoxins, and therefore increased transfer of endotoxin from the septic focus into the bloodstream, may also occur in cases of extensive Gram-negative infection such as peritonitis. Such a massive influx of endotoxins exhausts the plasma's capacity to inactivate these endotoxins quickly enough, leading to higher plasma levels of biologically active endotoxin and resulting in clinical endotoxemia. On the one hand, endotoxin causes the release of toxic mediators and on the other hand, it also disturbs the energy metabolism of the cell, resulting in cell death and release of more endotoxin. For this reason, all diseases involving the possibility of increased endotoxin transfer from the intestine or from a septic focus into the blood, or which involve a disturbance of the physiological elimination of endotoxin by the liver, require additional therapeutic and prophylactic measures capable of neutralizing endotoxin activity in the blood (Opal S M, The clinical relevance of endotoxin in human sepsis—a critical analysis. J. Endotoxin Res. 8:473-6, 2002).

An important additional therapeutic measure in treatment of endotoxemia is the reduction of the influx of endotoxins from the intestine, which is continuous under physiological conditions. Oral administration of substances capable of adsorbing endotoxin has been proposed as a therapeutic measure to reduce the influx of endotoxin from the intestine into the blood. The main problem involved in using these substances is that they succeed in binding the endotoxins in the intestine, but do not inactivate their toxic properties, so that toxic endotoxins might be released once again as a result of changes in the intestinal environment.

As demonstrated by clinical trials, it is possible to reduce plasma endotoxin activity by administering monoclonal lipid A antibodies. Plasma endotoxin activity can also be reduced to a certain degree by administering polyvalent immunoglobulin preparations containing a certain levels of antibodies to neutralize lipid A. With the exception of the preparations containing monoclonal lipid A antibodies, however, all of the therapeutic means available to date are marred by the disadvantage that they inactivate only a certain percentage of the endotoxins entering the blood. For this reason, they prove ineffective when larger amounts of endotoxins enter the bloodstream.

It is known that LF is active as a therapeutic agent to neutralize effects of endotoxin (U.S. Pat. No. 5,240,909). Lactoferrin binds to lipid A, the toxic moiety of LPS, with high affinity (Appelmelk B J et al., Lactoferrin is a lipid A binding protein. Infect Immun 62:2628-2632, 1994). Interaction of LPS with monocytes/macrophages results in the production and release of TNF-α which plays an important role in the induction of septic shock. Lactoferrin binding to lipid A competitively neutralizes LPS interactions with monocytes/macrophages. In this process, however, LF also gets depleted rapidly and may not be able to cope if the endotoxin is released in large quantities. Lactoferrin can also reduce the physiological influx from the intestinal tract into the bloodstream by inactivation/neutralization of the endotoxins released into the intestine tract while they are still inside the intestinal lumen (Caccavo D et al., Antimicrobial and immunoregulatory functions of lactoferrin and its potential therapeutic applications. J Endotoxin Res 8:403-17, 2002).

The pathobiological sequence of reactions mediated by endotoxin involves oxygen radicals. Among reactive oxygen species, hydroxy-radicals, either single or in combination with peroxynitrite, cause the tissue damage often observed during sepsis (Bhattacharya J et al., Mode of action of endotoxin—role of free radicals and antioxidants. Curr Med Chem 11:359-68, 2004). Natural antioxidants derived from plant extracts are widely known to protect against sepsis-mediated injury. Phyto-antioxidants, particularly polyphenolic compounds could effectively neutralize endotoxins (Davidson P M, Naidu A S Polyphenols, In 'Natural Food Antimicrobial Systems', ed. AS Naidu, pp. 265-294. Boca Raton: CRC Press, 2000). Polyphenols suitable for use in the teachings of the present invention include curcumin (turmeric root extract), carvacrol, thymol, borneol, catechol, camphor or oleuropein. Flavonoids are also known to inhibit the LPS-stimulated TNF-α and IL-6 proinflammatory molecules.

The antioxidant mode of action of oleoresins and aquaresins isolated from turmeric, ginger, clove and cinnamon has been extensively studied in free radical scavenging and anti-inflammatory protection. Morikawa et al. reported that an 80% aqueous acetone extract of curcumin (50 mg/kg) could inhibit endotoxin-induced serum elevation of transaminases and provide protection against TNF-α-induced liver injury (Morikawa T et al., Potent protective effects of sesquiterpenes and curcumin from Zedoariae Rhizoma on liver injury induced by D-galactosamine/lipopolysaccharide or TNF-α. Biol Pharm Bull 25:627-31, 2002). Chan et al. indicated that curcumin (2.5-10 µM) could also inhibit endotoxin and interferon-gamma induced nitrite production by mouse peritoneal cells by more than 50% (Chan M M et al., Effects of three dietary phytochemicals from tea, rosemary and turmeric on inflammation-induced nitrite production. Cancer Lett 96:23-29, 1995).

Oleuropein, the bitter principle of virgin olive, is also a potent antioxidant endowed with anti-inflammatory activity, a scavenger of superoxide radicals and an inhibitor of neutrophil respiratory burst in vivo (Viscoli F et al., Free radical-scavenging properties of olive oil polyphenols. Biochem Biophys Res Commun 247:60-4, 1998). Oleuropein (10 µM) has been shown to effectively inhibit copper sulfate-induced low-density lipoprotein (LDL) oxidation (Visioli F, Galli C, Oleuropein protects low-density lipoprotein from oxidation. Life Sci 55:1965-71, 1994).

Terpenes such as carvacrol [2-methyl-5-(1-methylethyl)-phenol], thymol [5-methyl-2-(1-methylethyl)-phenol] and 6-gingerol are also well known antioxidants. These monoterpenoids inhibit peroxidation of phospholipids in the presence of iron(III) and Vitamin C (ascorbate) as well as excellent scavengers of peroxyl radicals (Aeschbach R et al., Antioxidant actions of thymol, carvacrol, 6-gingerol, zingerone and hydroxytyrosol. Food Chem Toxicol 32:31-6, 1994).

Finally, flavonoids are the most studied natural antioxidants which are important constitutents of the non-caloric part of human diet with an average daily intake (ADI) of about 600 mg/day. The antioxidant activity of flavonoids is dependent on the number and arrangement of hydroxyl groups across their structure and the presence of electron-donating as well as electron-withdrawing substituents in their ring structure. In summary, these properties strongly establish flavonoids as excellent candidates to neutralize endotoxins.

The flavonoid group is mainly comprised of a range of $C_{15}$ aromatic compounds including, but not limited to, chalcones, dihydroflavones (flavanones), flavones, biflavonoids, dihydroflavonols, flavonols, anthocynidins and proanthocyanidin tannins, together with numerous derivatives are the glycosidic forms located in cell vacuoles of the plant (Naidu A S et al., Flavonoids, In 'Natural Food Antimicrobial Systems', ed. A S Naidu, pp325-48. Boca Raton: CRC Press, 2000; Bors W et al., Flavonoids and phytophenols—chemistry and biology. In 'Handbook of Antioxidants', ed. Cadenas E, Packer L, pp. 409-66. New York: Marcel Dekker, 1996). More lipophilic forms such as methylated, acylated and prenylated aglycones are found in or on the cuticular waxes, and biflavanoids are located in the cuticle. Grapes are rich source of flavonoids including flavan-3-ols, anthocyanins (in red grapes) and flavanols (Cheynier V, Rigaud J, HPLC separation and characterization of flavonols in the skins of *Vitis vinfera* var. *Cinsault*. Am J Enol Vitic 37:248-52, 1986). The specific flavonols found in grapes are all glycosides and include glycosides of myricetin, quercetin, kaempferol, and isorhamnetin. Additionally, green tea is abundant with several antioxidant isoflavonoids, particularly catechins, gallocatechins, epicatechins, epicatechin gallate, epigallocatechin, and epigallocatechin gallate (Yamamoto T et al., Chemistry and applications of green tea. New York: CRC Press, 1997). Lin et al. showed that 3-OH flavone, biacalein, kaemferol and quercetin are potent inhibitors of endotoxin-induced nitric oxide production by macrophages (Lin H Y et al., Inhibition of lipopolysaccharide-induced nitric oxide production by flavonoids in RAW264.7 macrophages involves heme oxygenase-1. Biochem Pharmacol 66:1821-32, 2003). Patil et al. reported that administration of flavonoids such as apigenin-7-glucoside (5-20 mg/kg) and quercetin (25-100 mg/kg) could reverse the endotoxin-induced retention deficits in a dose dependant manner (Patil C S et al., Protective effects of flavonoids against aging- and lipopolysaccharide-induced cognitive impairment in mice. Pharmacology 69:59-67, 2003). This neutralization activity was attributed to the ability of flavonoids to inhibit cyclooxygenase-2 and inducible nitric oxide synthase in vivo.

Phycocyanin, a biliprotein from the blue-green algae *Spirulina platensis*, and its chromophore phycocyanobilin, are potent antioxidants, free-radical scavengers and inhibitors of microsomal lipid peroxidation (Bhat V B, Madyastha K M, Scavenging of peroxynitrite by phycocyanin and phycocyanobilin from *Spirulina platensis*—protection against oxidative damage to DNA. Biochem Biophys Res Comm 285:262-6, 2001; Gemma C et al., Diets enriched in foods with high antioxidant activity reverse age-induced decreases in cerebellar beta-adrenergic function and increases in proinflammatory cytokines. J Neurosci 22:6114-20, 2002). *Spirulina maxima* is another microalga rich in phenolic acids, tocopherols, and beta-carotene which are effective antioxidants in vivo. *Spirulina* (5 mg/day for 2 weeks) could significantly down-regulate pro-inflammatory cytokines and decrease malondialdehyde levels. These properties establish the pigmented compounds of *Spirulina* as potent candidates for neutralizing endotoxins present in LF preparations.

In the TCR method of the present invention, microbial decontamination with surfactants occurs at the first tier and synergistic decontamination by LF itself results from detergent polarization effects at the this tier. Whereas in the second tier, the presence of antioxidants, in combination with an anion-rich environment generates a potential synergy with LF due to prooxidant-antioxidant effects and thereby could further eliminate both endotoxin and Gram-negative microbial contaminants in the resulting mixture. Finally, the polyphenols further neutralize the activity of endotoxin in LF at the third tier. All the tiers of decontamination activity generated in the TCR method of the present invention do not affect the viability or proliferation of probiotic LAB. On the contrary, the non-LF natural compounds used in creating this TCR system, such as turmeric root extract (curcumins), anthocyanins, oleuropeins and phycocyanins are known prebiotic compounds. Furthermore, the polyphenols used are also functional bioactive phytochemicals with specific health benefits.

Lactoferrin is known to interact with several target sites and co-factors in the intestinal tract such as heparin sulfate on the mucosal lining, enterocytes on intestinal epithelia, specific binding to subepithelial matrix proteins (e.g. fibronectin, collagens, laminin and vitronectin), complexing with immunoglobulin A and lysosyme. The bioavailability of LF supplements for useful prebiotic applications is dependant on the dose regimen of LF and the extent of unbound (free) LF in the intestinal lumen. Formulation of LF with slow-release and/or controlled-release mechanisms to avoid uni-directional equilibrium with LF-binding molecules that could circumvent the limited bioavailability of LF.

In one embodiment of the present invention, a prebiotic delivery system is provided in which prebiotic substances are formulated in solid, liquid or gel form with or without probiotic LAB. Dosages of LF in accordance with the teachings of the present invention range from 0.01 mg to 10.00 grams per day, preferably 1.00 mg to 250.00 mg per day.

In accordance with an embodiment of the present invention, the LF composition is in the form of a multi-layered coated tablet or capsule. If probiotics are included in the composition, the freeze-dried probiotic LAB are embedded in at least one core of the tablet in the form of granules and at least one shell structure is present containing (fdn)-LF with surfactants including, but not limited to, polysorbates, saponins, and bile salts; and antioxidants including, but not limited to vitamins and metal chelators together with substances adapted to create an anion-rich environment including, but not limited to, carbonates, bicarbonates, carbonated liquids and anaerobic encapsulation systems; and endotoxin neutralizing substances in permissible quantities such as polyphenols including, but not limited to, oleoresins, aquaresins, terpenes, flavonoids, and phycocyanins.

In another embodiment of the present invention, a sustained release delivery system is provided for the delivery of prebiotics and probiotics.

In yet another embodiment of the present invention, a method is provided to deliver the prebiotic by an enteral feeding device directly into the intestine and thereafter delivering the probiotic either orally or again through the enteral feeding device.

Pharmaceutically acceptable formulations of the prebiotic LF compositions made according to the teachings of the present invention contain at least one pharmaceutically acceptable carrier. As used herein, pharmaceutically acceptable carriers include any of the standard pharmaceutical carriers known to those of skill in the art. Pharmaceutically acceptable carriers include, but are not limited to, solvent(s), vehicle(s), adjuvant(s), excipient(s), binder(s), thickener(s), suspending agent(s) and filler substance(s) that are known to the skilled artisan suitable for administration to humans and/or non-human vertebrates. For example, useful carriers include, but are not limited to, solid, semisolid, or liquid carbohydrates such as glucose and sucrose, or polymeric substances like starch or dextran.

Useful carriers also include emulsifiers or suspending agents that are pharmaceutically acceptable and which can be used as vehicles for dispersion. Emulsifiers useful in embodiments of the present invention include, but are not limited to, monoglyceride compounds, diglyceride compounds, triglyceride compounds, glycerol, and phospholipids such as gum acacia, agar, petrolatum, lanolin, dimethyl sulfoxide (DMSO), normal saline (NS), phosphate buffered saline (PBS), sodium alginate, bentonite, carbomer, carboxymethyl-cellulose, carrageenan, powdered cellulose, cholesterol, gelatin, hydroxyethyl cellulose, hydroxypropyl cellulose, hydroxypropyl methylcellulose, methylcellulose, octoxynol 9, oleyl alcohol, polyvinyl alcohol, povidone, propylene glycol monostearate, sodium lauryl sulfate, sorbitan esters, stearyl alcohol, tragacanth, xanthan gum, chondrus, glycerin, trolamine, avacado oil, coconut oil, coconut butter, propylene glycol, ethyl alcohol, malt and malt extract.

In additional embodiments of the present invention, compositions also include bioactive agents, dietary supplements, nutraceuticals, functional foods, prophylactic agents and therapeutic agents, alone or in combinantion, in combination with prebiotic LF, to particularly suit the needs of the recipient. Bioactive agents suitable for use in the compositions of the present invention include, but are not limited to, immunoglobulins, lactoperoxidase, glycomacropeptide, conalbumin (ovotransferrin), lysozyme and avidin. Dietary supplements suitable for use in the compositions of the present invention include, but are not limited to, vitamins (including, but not limited to, A, C, D and E), B complex vitamins (including, but not limited to, $B_6$, $B_{12}$, thiamine, riboflavin, niacin and pantothenic acid), folic acid, biotin, enzymes, co-enzymes, amino acids, grape seed and skin extracts, cranberry extracts and minerals. Functional foods/nutriceuticals suitable for use in the compositions of the present invention include, but are not limited to, soy proteins, flaxseed oil, lycopenes, allicin/ajoene, catechins, omega fatty acids, yoghurt and fermented dairy products. Prophylactic agents suitable for use in the compositions of the present invention include, but are not limited to, vaccines, immune boosters and probiotic agents. Therapeutic agents suitable for use in the compositions of the present invention include, but are not limited to, antibacterial agents, antifungal agents, antiviral agents and antiparasitic agents.

Ultra-cleansed LF preparations made according to the teachings of the present invention are useful as physiologic delivery systems to deliver therapeutic and prophylactic agents to mammalian mucosal sites such as the gastrointestinal tract, the oropharyngeal region, the nasopharyngeal region, the vulvo-vaginal region and the skin.

Probiotic bacteria useful in embodiments of the present invention include physiologically effective dosages of at least one LAB strain, typically in the form of a freeze-dried powder, emulsion or viable or non-viable cell preparation, selected from a group consisting of, but not limited to, strains of bacteria of the genus *Lactobacillus* including *L. acidophilus, L. amylovorus, L. animalis, L. bavaricus, L. brevis, L. bulgaricus, L. casei* spp. *casei, L. casei* spp. *rhamnosus, L. crispatus, L. delbrueckii* ssp. *lactis, L. eichmanni, L. fermentum, L. helveticus, L. jensenii, L. kefir, L. paracasei, L. pentosus, L. plantarum, L. reuteri, L. salivarius* and *L. sake*; strains of bacteria of the genus *Leuconostoc* including *Leu. cremoris* and *Leu. lactis*; strains of bacteria of the genus *Bifidobacterium* including *B. adolescentis, B. animalis, B. bifidum, B. breve, B. infantis, B.*

*longum*, and *B. thermophilum*; strains of bacteria of the genus *Pediococcus* including *Ped. acidilactici* and *Ped. pentosus*; strains of bacteria of the genus *Peptostreptococcus* including *Pep. Assacharolyticus* and *Pep. productus*; strains of bacteria of the genus *Propionibacterium* including *Pro. acidipropionici*, *Pro. freudenreichii*, *Pro. jensenii* and *Pro. theonii*; strains of bacteria of the genus *Streptococcus* including *Strep. cremoris*, *Strep. faecium*, *Strep. lactis*, *Strep. Raffinolactis* and *Strep. thermophilus*.

Dosages of probiotic bacteria contained in the compositions of the present invention comprise bacterial counts in the range of $10^2$ to $10^{12}$ colony forming units (for viable LAB) or microbial cells (for non-viable LAB). Optimal dosages of probiotic bacteria contained in the compositions of the present invention comprise bacteria counts in the range of $10^5$ to $10^{10}$ colony forming units (for viable LAB) or microbial cells (for non-viable LAB). Colony forming units are defined as total number of viable bacteria grown on agar medium.

Optionally, the prebiotic LF compositions of the present invention may contain dietary supplements, vitamins, amino acids, protein or starch hydrolysates and flavorants. A flavorant can be a natural extractive of a spice plant or herb, for non-limiting example, rosemary, sage, basil, oregano or any other pleasant herbal or fruity flavorants or mixture of flavorants. Synthetic flavorants are also suitable. The flavorant can also have antimicrobial properties.

The compositions of the present invention containing prebiotic LF in suitable pharmaceutically acceptable formulations are useful for administering to humans, including children and infants (i.e., pediatric uses) and non-human vertebrate animals. The compositions are formulated for acceptable delivery to a human or non-human vertebrate gastrointestinal tract or other body site or tissue.

Compositions of the present invention intended for an oral delivery route may be prepared according to any method known to the art for the manufacture of pharmaceutical compositions. Compositions may also be coated by the techniques described in U.S. Pat. Nos. 4,256,108, 4,160,452 and 4,265,874 which are incorporated herein by reference for all that they contain regarding the formulation of osmotic therapeutic tablets for controlled release. Other techniques for making controlled release compositions can be used in the formulation of the compositions of the present invention, such as those described in the U.S. Pat. Nos. 4,193,985, 4,690,822 and 4,572,833, incorporated herein by reference for all that they contain regarding methods of making controlled release compositions.

An embodiment of the present invention, a pharmaceutical composition is formulated for a non-systemic ingestive delivery system, such as, but not limited to a tablet, capsule or caplet. For the purposes of the present invention, a non-systemic ingestive delivery system refers to an oral delivery system wherein the contents of the delivery system do not reach the bloodstream. The non-systemic ingestive delivery system of the present invention can optionally include an enteric coating to prevent esophageal or gastric release of LF. Such enteric-coated compositions disintegrate after leaving the stomach, resulting in drug dispersion in the small intestine or colon where LF acts topically at the intestinal mucosa. As the skilled artisan will be aware, controlled release or enteric-coated drug delivery systems typically involve pH-sensitive, polymer-coated tablets, capsules or caplets. A polymer coating can be selected that will direct release of a composition containing LF to a particular region of the gastrointestinal tract. Such polymers include, but are not limited to, acrylic polymers such as Eudragit®-L or Eudragit®-S, and cellulosic polymers, such as ethylcellulose.

In a non-limiting example, amphionic ethylcellulose dissolves at either acidic or basic pH to release the composition it contains. In another non-limiting example, the acrylic polymer coating Eudragit®-S is degraded at pH levels above pH 7.0. Thus, it is carried to the portion of the gastrointestinal tract where intraluminal pH is elevated above 7.0, after passing through the far more acidic environment of the stomach, and as a result, the composition containing LF is reliably released in the distal small intestine (ileum) and colon of a human recipient. Another example of a controlled release formulation useful with the compositions of the present invention is a composition coated first with a semi-permeable layer of ethylcellulose and second with an acrylic polymer, such as Eudragit®-L, which is degraded at pH levels above pH 5.6 in the distal small intestine and colon to release and deliver the composition there (Dew M J et al., An oral preparation to release drug in the human colon. Br J Clin Pharmacol 14:405-8, 1982).

In additional embodiments of the present invention, tablets, capsules or caplets of the desired composition can be formulated with multiple layers of coatings for slow release over an extended period as known in the art.

In another embodiment of the present invention, a tablet or a patch for delivery through the oral mucosa can comprise an inner layer containing the therapeutic agent of choice, a permeation enhancer, such as a bile salt or fusidate, and a hydrophilic polymer including, but not limited to, hydroxypropyl cellulose, hydroxypropyl methylcellulose, hydroxyethyl cellulose, dextran, pectic, polyvinyl pyrrolidone, starch, gelatin, or any number of other polymers known to be useful for this purpose. This inner layer can have one surface adapted to contact and adhere to the moist mucosal tissue of the oral cavity and may have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. These examples are merely illustrative of available transmucosal delivery technology and are not limiting of the present invention.

Another embodiment of the present invention provides compositions employing a pharmaceutically acceptable non-systemic delivery route such as a suppository or foam for delivery of a composition including LF for delivery via urogenital structures, anus or rectum. Once delivered, the LF of the present invention will act topically at the intestinal mucosa. Such suppository or foam delivery systems are known in the art. These LF formulations for delivery via urogenital structures, anus or rectum can employ a variety of conventional thickeners or suspenders including, but not limited to alginate, xanthan gum, lanolin, or petrolatum. Also contemplated are suppositories or foams comprising hydrophilic polymers including, but not limited to, hydroxypropyl cellulose, hydroxypropyl methylcellulose, hydroxyethyl cellulose, dextran, pectin, polyvinyl pyrrolidone, starch, gelatin, or any number of other polymers known to be useful for this purpose.

In an embodiment of the present invention, the composition is a gel formulated for delivery of LF via the rectal or vaginal mucosa, similar to gels commonly used for the delivery of various other therapeutic agents. Hydrogel matrices known for this purpose have been described in U.S. Pat. No. 4,925,677 incorporated herein by reference for all it contains regarding hydrogels. Such biodegradable gel matrices may be formed, in a non-limiting example, by cross-linking a proteinaceous component and a polysaccharide or mucopolysaccharide component, then loading with LF for delivery over an extended period.

Another embodiment of the present invention comprises a lavage system, whereby a recipient will ingest a large volume of an osmotically balanced flushing solution, containing LF, or a conventional flushing solution in conjunction with another ingestible form of LF antimicrobial agent. Such a lavage system can virtually eliminate harmful bacterial populations from the intestine. This may be especially desirable in refractory cases of bacterial overgrowth or in preparing a patient for abdominal surgery. Commercially available lavage or enema solutions, such as Golyte or Fleet® Phospho-soda® preparations can be used as carriers to formulate the composition of the present invention. A lavage or enema solution is optionally combined with one or more antibiotic(s) or other antimicrobial agent(s) (Vanderhoof J A et al., Treatment strategies for small bowel bacterial overgrowth in short bowel syndrome. J Pediatr Gastroenterol Nutr 27:155-60, 1998).

In another embodiment of the present invention, an ingestive delivery system is provided which is useful for veterinary applications. In this embodiment, a pharmaceutical preparation of the present invention is formulated and prepared for ingestion by an animal along with its food, as part of a pharmaceutically acceptable feed mixture. A pharmaceutically acceptable food additive or supplement for humans is also contemplated. In an embodiment of the present invention, LF-containing compositions can be added to a foodstuff.

In an embodiment of the present invention, the LF is delivered in conjunction with a probiotic LAB. The LAB is delivered in a pharmaceutically acceptable ingestible formulation, such as in a capsule, or for some subjects, consuming a food supplemented with a composition of the present invention. Non-limiting examples of foods suitable for use with the LF of the present invention include milk, yoghurt, cheese, meat and other fermentable food preparation.

We now turn to a detailed description of several non-limiting embodiments of the present invention related to treatment for contaminant reduction processes for the removal of microorganisms and bacterial degradation products such as endotoxin prior to the use of the cleansed LF as the physiologic delivery system of the present invention.

The bioburden of different LF preparations (whey-derived and milk-derived) was measured by standard assays according to the United States Food and Drug Administration (FDA) Bacteriological Analytical Manual (BAM) Revision-A. Briefly, 1 g of LF is dissolved in 100 mL of 0.9% sterile saline solution. After preparing 10-fold serial dilutions, samples were tested by both pour plating (1 mL) and surface plating (0.1 mL) methods. Enumeration of total aerobic bacteria was performed by using Plate Count Agar (PCA) (Difco Laboratories, Detroit, Mich.). Total coliform bacteria were enumerated by using violet red bile agar (VRBA) containing 1% glucose (Difco). Lactic acid bacteria were enumerated using daMan, Rogosa, and Sharpe (MRS) broth containing 1.5% agar and 0.02% sodium azide (Difco). Yeasts and molds were enumerated using PCA containing chlortetracycline HCl and chloramphenicol, 100 μg/mL. Plate Count Agar (for total aerobic bacteria) and VRBA plates were incubated at 35° C. PCA (for yeast and molds) and MRS plates were incubated at 30° C. VRBA plates were read after 24 h, PCA and MRS plates after 48 h, and PCA plates for yeast and mold growth were read after 72, 96 and again after 120 h.

Bacterial endotoxin (LPS) contamination in the LF protein preparations was quantified by *Limulus Amoebocyte* Lysate (LAL) assay using a FDA approved QCL-1000 test kit (Cambrex Bioscience Walkerville). Briefly, a 0.1% LF solution prepared in pyrogen-free water was serially diluted in a 96-well microplate with pyrogen-free water and incubated for 5 min at 70° C. with constant shaking. Endotoxin levels in the protein solution was measured with the QCL-1000 colorimetric assay according to the manufacturer's instructions. Endotoxin in the reaction mixture forms yellow color and is measured photometrically at 405-410 nm. Standard endotoxin (Cambrex cat. No. E50-640) was used as a positive control. QCL-1000 is a rapid assay with a 16 min quantitative end point and its sensitivity ranged from 1.0 to 0.1 endotoxin units (EU)/mL.

Binding of endotoxin to phagocytic cells (neutrophils, monocytes or macrophages) results in production of robust quantities of cytokines, especially tumor necrosis factor alpha (TNF-α). Therefore, measurement of TNF-α production in phagocytic cells exposed to LF samples is an indirect measurement of the endotoxin activity. THP-1 cells ($10^6$/mL), a monocytic cell line were incubated with LF samples (diluted in RPMI media). At different time intervals (1 to 12 h), test solutions were collected, cell debris removed by low-speed centrifugation (5000×g for 10 min) and clarified supernatants (in triplicate) were assayed for TNF-α activity using the specific DuoSet ELISA development system (R&D Systems, Minneapolis, Minn.) according to the manufacturer's instructions. Purified LPS from *E. coli* was used as a positive control and pyrogen-free water served as a negative control.

According to the microbiological analysis, whey-derived LF harbored more bio-burden than the milk-derived LF. A significant portion of aerobic plate counts of whey-derived LF were identified as Gram positive microorganisms. The whey-derived LF contained more mold contaminants such as *Pencillium* spp. and *Aspergillus* spp., while milk-derived LF showed contamination with species of yeast. Two samples of whey-derived LF also showed the presence of type-1 fimbriated *E. coli* pathogens.

The endotoxin levels of both commercial LF preparations reflected their coliform and Gram negative bacterial loads. The median endotoxin levels in whey-derived LF were about 20× times higher than in the milk-derived LF. The endotoxin contaminants in both LF preparations were biologically active and induced TNF-α production in stimulated monocytes.

Table 1 presents data on the types and extent of contamination in bulk-produced LF preparations. These data clearly demonstrate the necessity to develop novel treatment(s) for contaminant reduction in LF preparations, especially if the LF is intended for human use.

TABLE 1

Bioburden and endotoxin contaminants in commercial LF preparations

| | MEDIAN VALUE (MIN-MAX RANGE) | |
|---|---|---|
| ANALYSIS | Whey-derived LF (n = 10) | Milk-derived LF (n = 15) |
| Aerobic Plate Count (APC) | 2230 (395-9750) CFU/g | 116 (5-2448) CFU/g |
| Total Coliforms | 36 (4-119) CFU/g | 5 (0-98) CFU/g |
| Yeast & Mold count | 19 (1-37) CFU/g | 3 (0-18) CFU/g |
| *Escherichia coli* | 6 (0-21) CFU/g | 0 (0-2) CFU/g |
| *Staphylococcus aureus* | 0 (0-16) CFU/g | 0 (0-5) CFU/g |
| Endotoxin levels (LAL assay) | 430 (72-1056) ng/g | 21 (6-112) ng/g |
| Endotoxin (TNF-α) activity | 3440 (648-7920) pg TNF/g | 126 (45-896) pg TNF/g |

Several natural compounds with nutraceutical benefits and proven safety [i.e. generally recognized as safe (GRAS) status from US-FDA] in mammalian host systems have been screened for functional compatibility and use in the TCR process of the present invention with LF preparations. Commercial LF (whey or milk-derived preparations) with inherent bioburden or challenged with contaminants or specific milk-borne human pathogens, were subjected to different TCR steps. The microbial contaminant populations that were targeted in LF broadly included aerobic bacteria (consisting of both Gram positive and Gram negative bacteria, coliforms, yeast and molds; whereas the specific pathogen challenge included *E. coli* serotype O157:H7, *Salmonella typhimurium, Listeria monocytogenes*, and *Staph. aureus*. The efficacy of TCR processes to reduce and/or neutralize the inherent and externally challenged endotoxin contamination was also measured.

Based on the types and levels of contaminants, as well as the microbiological quality assurances implemented with cGMPs in the bulk manufacturing of LF, a multi-tier TCR process has been developed using, natural substrates as decontaminant agents. In non-limiting examples, the TCR process can be used as a stand alone technology or could be integrated with different lab-scale, pilot-scale or commercial-scale technologies practiced in the isolation and purification of LF.

One embodiment of the present invention discloses a method for preparing a mixture composition to circumvent different microbial contamination problems-associated with the commercial LF described herein. Accordingly, this method consisting of a multi-tier approach to contaminant exclusion could facilitate an effective in vivo use of commercial LF preparations for multifunctional applications not limited to the prebiotic purposes.

The method of the present invention includes the creation of a surfactant environment analogous to the physiological gastric detergents to selectively disrupt the cell membranes of any contaminant microorganisms. Natural and/or food-grade surfactants for use in the present invention include plant-derived saponins such as extracts from *quillaya* (*Quillaya saponaria*), *yucca* (*Yucca schidigera*), soy (*Glycine max*), green tea (*Camelia sinensis*), ginseng (*Panax ginseng*), and *fenugreek* (*Trigonella faenum-graecum*), food-grade polysorbates; animal-derived bile salts from bovine and porcine gut, in sufficient concentration to prevent the proliferation of microbial contaminants either alone or in combination.

Accordingly, the present invention utilizes carbonate or bicarbonate anions at specific ratios in combination with natural antioxidants such as vitamin A, vitamin C, vitamin E and metal chelators to enhance the anion-dependent LF bioactivity. For the purpose of restoring the anion-dependant bioactivity of commercial LF, methods related to generating carbonated aqueous systems or anaerobic encapsulations are also suitable.

This invention further teaches the use of effective and permissible amounts of food-grade phytochemicals (polyphenols) to neutralize endotoxin contaminants in commercial LF preparations in the third tier of the method of the present invention. Polyphenols of particular use for this purpose include, but are not limited to, oleoresins (eg. curcumin, borneol and thymol), aquaresins (eg. extracts of turmeric, ginger, clove and cinnamon), oleuropeins (eg. virgin olive extracts), terpenes (eg. piperine, camphor, carvacrol, 6-gingerol and tree-tea oil), flavonoids (eg. extracts of cranberry, grape skin and green tea) and biliproteins (eg. phycocyanins such as *spirulina*

Methods for purification and isolation of LF from diverse sources exist and certain technologies are currently practiced in commerce as cited in the U.S. Pat. Nos. 4,190,576, 4,436,658, 4,667,018, 4,668,771, 4,791,193, 4,997,914, 5,087,369, 5,149,647, 5,169,936, 5,179,197, 5,516,675, 5,571,896, 5,596,082, 5,756,680, 5,849,885, 5,861,491, 5,919,913, 6,010,698, 6,096,870 and 6,268,487 which are incorporated by reference herein for all that they disclose regarding methods for purification and isolation of LF from diverse sources.

A flow chart representing the steps of the TCR process of the present invention is schematically represented in FIG. 1. Furthermore, any possible points of integrating different tiers of TCR process of the present invention has been exemplified in FIG. 1. Lactoferrin from a variety of sources including, but not limited to, recombinant LF, colostrum, milk and whey, is first subjected to surfactant treatment (tier one) in to disrupt contaminant cell membranes. Colostrum and milk sources of LF first undergo a centrifugation or precipitation step before surfactant treatment. The recombinant-derived LF undergoes extraction including phase partitioning and/or protein fishing after surfactant treatment. The whey-derived LF also has a post-surfactant first tier step of acid neutralization.

After a selective surfactant treatment (tier one), LF from all sources is subjected to similar decontamination treatment processes. The decontamination steps consist of antioxidant treatment (tier two) and polyphenol treatment (tier three) prior to the chromatographic separation, elution and desalting of the LF. An additional round of antioxidant and polyphenol treatment is incorporated along with endotoxin removal using commercial kits or passage over an LF affinity column. The purified LF-TCR is then dried by a method including, but not limited to, spray-drying or freeze drying. The purified LF-TCR is then ready for use as a prebiotic or as a physiologic delivery system according to the teachings of the present invention.

Sources of whey-derived LF and certain recombinant LF often contain a high bioburden of Gram positive microflora and spore-forming organisms. Therefore, the surfactant tier of the TCR process of the present invention can be added to the start material. Additionally, the surfactant tier of the TCR process is effective on sources of LF such as milk-derived LF and colostrum-derived LF after the separation of serum from the dairy solids or precipitates.

All three tiers of the TCR process or the combination of antioxidant and polyphenolic tiers can be incorporated in the process prior to the chromatographic purification of LF. The surfactants, antioxidants and polyphenolics added during the TCR process can be removed from the LF protein after their effective antimicrobial and detoxification performance and during the chromatographic elution and desalting (i.e. ultra-filtration) procedures.

The combined antioxidant and polyphenolic tiers can also be incorporated in the TCR process after the isolation/purification of LF and prior to the protein drying process. This addition of steps to the TCR process can be further integrated with commercial endotoxin-removal technologies such as EndoTrap®e, Detoxi-Gel™ Endotoxin Removing Gel, Affi-Prep® Polymyxin Matrix, Matrex® Cellufine™ Sufate and Vivapure®.

EndoTrap® (Profos A G, Regensberg, Germany) can be used either in batch or column mode. In general, removal of high endotoxin levels is more practical in the column mode while low endotoxin levels are more efficiently removed in batch processing. However, parameters such as pH, ionic strength, temperature and contact time have to be optimized for each application to obtain maximum endotoxin removal with minimum loss of product.

Detoxi-Gel™ Endotoxin Removing Gel (Pierce, Rockford, Ill.) uses immobilized polymixin B to bind and remove pyrogens (endotoxin) from solutions. Polymixin B neutralizes the biological activity of endotoxins by binding to the lipid A moiety of the bacterial lipopolysaccharide (endotoxin). Good chromatographic techniques are critical for optimal performance and the most effective removal of endotoxin will result if the gel is used in a column format than a batch method.

Affi-Prep® Polymyxin Matrix (Bio-Rad Laboratories, Hercules, Calif.) consists of a polymeric macroporous beads with USP Grade polymyxin B covalently attached. For optimum performance, this affinity column should be used in a dust-free enviroment.

Matrex® Cellufine™ Sulfate (Millipore Corporation,) consists of a rigid spherical cellulose matrix of 3 kD exclusion limit. This low density cation exchanger provides affinity binding for proteins such as LF, whereas endotoxins pass through the column unbound. Elution of bound product is effected through simple stepwise or gradient increases in the ionic strength of the elution buffer.

Vivapure® centrifugal ion exchange membrane devices (Cambridge Antibody Technology, Cambridge, UK) can be used for endotoxin removal. Clearance of endotoxin using this method is performed with a high conductivity buffer to prevent the need for any diafiltration into low salt buffers prior to the anion exchange.

Removal of endotoxin is one of the most difficult downstream processes during protein purification. Many commercially available products have limitations to remove endotoxin satisfactory, or require time consuming incubation steps. In many cases, complete endotoxin removal is only achieved with massive product loss. Therefore, based on the desired scheme for LF purification process, a compatible downstream process for endotoxin removal should be selected.

Lactoferrin can bind and neutralize endotoxins (Miyazaki K et al., Lactoferrin-lipopolysaccharide interactions. J Immunol 146:723-9, 1991; Elass-Rochard E et al., Lactoferrin-lipopolysaccharide interaction: involvement of the 28-34 loop region of human lactoferrin in the high-affinity binding to *E. coli* 055B5 lipopolysaccharide. Biochem J 312:839-45, 1995). The use of LF as an endotoxin neutralizing agent has been described in U.S. Pat. Nos. 5,240,909, 6,333,311 and 6,399,570 which are incorporated herein by reference for all they disclose regarding the use of LF as an endotoxin removal agent.

Therefore, the present invention provides TCR processes for endotoxin removal that bypass the use of commercial endotoxin-removal methods by using an affinity column cross-linked with LF prepared according to the teaching of the present invention. The TCR process provides natural materials with valued-added nutraceutical benefits including LF preparations that can be admixed with specific amounts of other TCR processed compounds to yield compositions exhibiting multifunctional properties. The steps involved in the TCR process and certain effective ingredients are described in the following examples.

EXAMPLE 1

TCR Process

A 1% (v/v) polysorbate-80 solution, a 0.5% solution of vitamin C (as calcium-L-ascorbate) with 10 mM sodium bicarbonate and 95% (w/v) turmeric root extract (0.1% curcumin) were used in the TCR process as surfactant, antioxidant and polyphenolic tiers, respectively.

Experiment 1: Ten grams of commercial whey-derived LF powder with a bioburden of 7200 CFU/g was dissolved in 100 mL of polysorbate-80 solution with gentle stirring at room temperature for 2 h. Quadruplicate samples of 10 mL each were aspirated from the homogenate and tested for bioburden according to the BAM protocol. The polysorbate-80 surfactant in the presence of LF caused about a 35% reduction in aerobic plate count (APC) and 40% reduction in yeast/mold counts. However, in this solution the coliform counts and the endotoxin activity in the LF remained unaffected.

Experiment 2: Ten minutes after adding 10 g LF to polysorbate-80 (100 mL) the solution was mixed with calcium-L-ascorbate (0.5 g) and 10 mM sodium bicarbonate and stirred at room temperature for 2 h. Quadruplicate samples of 10 mL each were aspirated from the homogenate and tested for bioburden according to the BAM protocol. The surfactant and antioxidant combination treatment of LF resulted in >95% reduction in APC and totally eliminated the coliforms as well as the yeast/mold populations. The endotoxin activity (measured as TNF-α production) in LF was reduced by about 40%.

Experiment 3: Ten minutes after adding 10 g LF to polysorbate-80 (100 mL) and adding the antioxidant tier as in Experiment 2, a polyphenolic phase was included with the addition of 1% curcumin to the solution with continuous stirring at room temperature for 2 h. Quadruplicate samples of 10 mL each were aspirated from the homogenate and tested for bioburden according to the BAM protocol. In the LF sample containing surfactant, antioxidant and polyphenolic tiers, the APC was markedly reduced by more than 99.9% and the endotoxin activity was greatly diminished almost to undetectable level.

Table 2 summarizes the results from the above three experiments. These experiments were performed with a single source of LF (whey-derived) with a high intrinsic load of microbial and endotoxin contaminants. Briefly, the TCR process consisting of a three tier system of surfactant, antioxidant and polyphenolic tiers effectively eliminated and/or neutralized the microbial and endotoxin contaminants in a sequentially progressive manner to provide an ultra-clean LF preparation.

TABLE 2

Efficacy of the TCR process on intrinsic contaminant populations in whey-derived LF

| TIER | TCR PROCESS | CONTAMINANT ACTIVITY | | | |
|---|---|---|---|---|---|
| | | APC (CFU/g) | Coliforms (CFU/g) | Yeast & Mold (CFU/g) | Endotoxin Activity (pg TNF/g) |
| 0 | Starting quality | 7200 | 96 | 25 | 5400 |
| I | Surfactant-phase (Polysorbate-80) | 4650 | 92 | 15 | 5375 |
| II | Antioxidant-phase (Vitamin C) | 260 | 0 | 0 | 3160 |

TABLE 2-continued

Efficacy of the TCR process on intrinsic contaminant populations in whey-derived LF

| TIER | TCR PROCESS | CONTAMINANT ACTIVITY | | | |
|---|---|---|---|---|---|
| | | APC (CFU/g) | Coliforms (CFU/g) | Yeast & Mold (CFU/g) | Endotoxin Activity (pg TNF/g) |
| III | Phytophenolic-phase (Turmeric root extract) | <10 | 0 | 0 | <1 |

EXAMPLE 2

Evaluation of TCR Process on Different Types of LF

The efficacy and possible broad-scale application of the TCR process to reduce the bioburden from different commercial types of LF (bovine LF derived from milk and whey; recombinant human LF expressed in a plant system) was evaluated. The TCR process consisted of the three tier system and the experiments were performed as described in Example 1. The TCR process results were expressed as cumulative endpoint data, consolidating the contaminant reductions in all three tiers.

In addition to treating the intrinsic contaminant loads, the efficacy of the TCR process was also tested against LF preparations challenged with specific pathogens. Accordingly, the milk- and whey-derived LF were challenged with an APC cocktail (~5-log CFU/g) consisting of *E. coli* ATCC43895 (3-log CFU/g), *Staph. aureus* ATCC25923 (3.5-log CFU/g) and *Listeria monocytogenes* ATCC19115 (3.2-log CFU/g) and subjected to the TCR process.

Table 3 summarizes the results of this study. The intrinsic bioburden was estimated at about a five-log load in the recombinant human LF, which was 2× and 10× times higher contamination level than the whey- and milk-derived bovine LF (bLF) preparations, respectively. Therefore, the challenge studies were performed with bovine LF at 5-log bacterial density. The TCR process effectively decontaminated the intrinsic bioburden and successfully reduced the pathogen challenge in all types of LF preparations.

TABLE 3

Efficacy of the TCR process on different LF preparations with intrinsic bioburdens and pathogen challenge

| LF source | TCR Process | BIOBURDEN (CFU/g) | | | | | |
|---|---|---|---|---|---|---|---|
| | | APC | Coliform | Yeast/Mold | *E. coli* | *S. aureus* | *Listeria* |
| Milk-bLF (Commercial) | Start | 760 | 20 | 11 | 0 | 0 | 0 |
| | Endpoint | <10 | 0 | 0 | 0 | 0 | 0 |
| Milk-bLF (Challenged) | Start | 18500 | 2400 | 450 | 958 | 3670 | 2350 |
| | Endpoint | 15 | 0 | 0 | 0 | 0 | <10 |
| Whey-bLF (Commercial) | Start | 5100 | 80 | 22 | 4 | 0 | 0 |
| | Endpoint | <10 | 0 | 0 | 0 | 0 | 0 |
| Whey-bLF (Challenged) | Start | 21600 | 1650 | 320 | 1200 | 3500 | 1950 |
| | Endpoint | 45 | <10 | 0 | 0 | 2 | 13 |
| Human LF (Recombinant) | Start | 9400 | 45 | 290 | 12 | 0 | 0 |
| | Endpoint | <10 | 0 | 0 | 0 | 0 | 0 |

Furthermore, the efficacy of the TCR process to neutralize endotoxin activity from different commercial types of LF (bovine LF derived from milk and whey; recombinant human LF expressed in a plant system) was evaluated. The TCR process consisted of a three tier system and the experiments were performed as described in Example 1. The neutralization of endotoxin at each tier of the TCR process is expressed as the reduction (%) in TNF-α induction of stimulated monocytes.

Table 4 summarizes the results of this study. The intrinsic endotoxin activity was about 12 ng/g in the recombinant human LF, which was 1.5× and 13× times higher than the whey- and milk-derived bovine LF preparations, respectively. The surfactant-tier of the TCR process did not affect the endotoxin activity. However, the antioxidant-tier elicited about a 40-60% reduction in the intrinsic endotoxin activity of the different LF preparations. Finally, the polyphenolic tier was highly potent and effectively neutralized >99.9% of endotoxin activity in all types of LF preparations. Put together, the TCR process has demonstrated a high degree of detoxification of intrinsic pyrogens in commercial LF preparations.

TABLE 4

Efficacy of the TCR process to neutralize endotoxin activity in different LF preparations

| TCR Process | TNF-α PRODUCTION in pg/g (% Reduction) | | |
|---|---|---|---|
| | Whey-derived bLF | Milk-derived bLF | Recombinant hLF |
| Starting material | 7920 | 896 | 11590 |
| Surfactant-tier (Polysorbate-80) | 7909 (0.1%) | 896 (0.0%) | 11585 (0.1%) |
| Antioxidant-tier (Vitamin C) | 4680 (40.9%) | 375 (58.1%) | 4490 (61.2%) |
| Polyphenolic-tier (Turmeric root extract) | <1 (>99.9%) | <1 (>99.9%) | <10 (99.9%) |

EXAMPLE 3

Functional Analysis for Prebiotic Activity of LF after TCR

The formulation composition is known to exert a significant effect on the structure-functional properties of LF. Therefore, the effects of the TCR process on the multifunctional activities of LF was evaluated. Accordingly, a functional analysis was performed with LF after TCR (LF-TCR) with respect to its prebiotic effects on lactic acid bacteria, antioxidant activity in combination with components of the TCR process and safety/toxicity by measuring cellular apoptosis upon exposure. The functional analysis data was compared with LF preparations prior to the TCR process, i.e. untreated controls.

The growth-multiplication of 18 different probiotic LAB (including three strains of *Bifidobacterium* spp., 13 strains of *Lactobacillus* spp., one strain each of *Lactococcus* spp., and *Streptococcus* spp.) was measured in the presence of LF-TCR and compared with untreated LF and controls (without any LF exposure). Two different methods of bacterial growth measurements were used in evaluating the prebiotic activity of LF-TCR.

Method 1—Growth impedance detection assay (GIDA): Microbial metabolism cause electrical charge alterations in cultivation media due to breakdown of nutrients. A Bactometer® Microbial Monitoring System Model-128 (bioMerieux Vitek, Hazelwood, Mo.) was used to monitor the growth of probiotic lactic acid bacteria (LAB) by measuring impedance signals (a function of both capacitance and conductance) in the cultivation media. The GIDA was performed in 16-well modules. Briefly, a volume of 0.5 mL double-strength Bactometer® broth (2×BB; general purpose culture medium for Bactometer®) was added to each well. A volume of 0.25 mL of LF-TCR sample followed by 0.25 mL of bacterial suspension ($10^4$ cells/mL) prepared in 0.9% saline was added to the wells. Addition of 0.5 mL saline or bacterial suspension to module wells with 0.5 mL 2×BB served as controls for sterility and growth, respectively. The inoculated modules (final volume of 1 mL) were incubated at 32° C., and impedance changes in the media was continuously monitored by the Bactometer® at 6 min intervals for 48 h. Bacterial growth curves were graphically displayed as percent changes of impedance signals versus incubation time. The amount of time required to cause a significant deviation from the baseline impedance was defined as the detection time (DT). If the DT value of a LF test sample was lower than the control, the LF test sample was considered to have a prebiotic effect.

Method 2—Micro-scale optical density assay (MODA): This tubidometric assay was used to measure microbial growth in vitro. The ability of LF or a test compound to inhibit microbial pathogens (antibiotic effect) or to promote the growth of probiotic LAB (prebiotic effect) can be measured by MODA. Briefly, 0.1 mL of sterile double strength (2×) deMann Rogosa Sharpe (MRS) broth was added to each well of a 96 well sterile microtiter plate (Costar® 3596, Corning, N.Y.). A 0.05 mL volume of test sample was added to designated wells followed by inoculation with 0.05 mL of a microbial cell suspension containing ~$10^5$ cells/mL (diluted from an optically pre-calibrated (OD 1.0 at 600 nm) solution of $10^9$ cells/mL). After inoculation, the microplate was incubated at 37° C. and the microbial growth was monitored at different time points as turbidity change in culture media by measuring OD at 600 nm using a microplate reader (VersaMax, Molecular Devices, Sunnyvale, Calif.). Prior to OD measurement, the contents of each microplate well was mixed for uniform suspension of microbial cells in the media. Wells containing broth without microbial inoculum served as the sterility control. Wells containing broth medium inoculated with microorganism, but without any test compound served as positive growth control. The MODA results are expressed as the percent of microbial growth in the test well relative to the microbial growth in the positive control well. The positive control well is considered to be 100% growth.

Milk-derived LF and its TCR processed LF protein were tested at 0.5% (w/v) concentration for prebiotic activity. The average GIDA detection time for probiotic LAB test strains (n=18) was estimated at 15.7 h. This detection time was shortened by 4.5 h by LF-TCR in comparison to 2.2 h by its original source of LF. According to the MODA, the growth-multiplication of probiotic LAB test strains (n=18) was enhanced by >100% with LF-(tcr), which was at least twice as effective in it's prebiotic ability than it's LF (untreated) counterpart with approximately 40% growth-enhancement. Data listed in Table 5 with different LAB strains clearly indicates that LF-TCR a powerful prebiotic agent.

TABLE 5

Growth-multiplication of probiotic LAB strains in the presence of 0.5% LF-TCR

| | PREBIOTIC ACTIVITY | | | | |
|---|---|---|---|---|---|
| | GIDA - Detection Time (h) | | | MODA - Growth (%)* | |
| PROBIOTIC (LAB) TEST STRAIN | Control | LF | LF-(tcr) | LF | LF-(tcr) |
| *Bifidobacterium bifidum* ATCC15696 | 19.5 | 17.8 | 15.1 | 142% | 210% |
| *Bifidobacterium infantis* ATCC15697 | 21.3 | 19.4 | 17.0 | 150% | 225% |

TABLE 5-continued

Growth-multiplication of probiotic LAB strains in the presence of 0.5% LF-TCR

| | PREBIOTIC ACTIVITY | | | | |
|---|---|---|---|---|---|
| | GIDA - Detection Time (h) | | | MODA - Growth (%)* | |
| PROBIOTIC (LAB) TEST STRAIN | Control | LF | LF-(tcr) | LF | LF-(tcr) |
| *Bifidobacterium longum* ATCC15707 | 19.0 | 16.9 | 14.5 | 148% | 205% |
| *Lactobacillus acidophilus* ATCC4356 | 12.6 | 11.0 | 8.7 | 132% | 189% |
| *Lactobacillus amylovorus* ATCC33620 | 17.9 | 17.0 | 15.1 | 121% | 165% |
| *Lactobacillus brevis* ATCC14869 | 18.2 | 15.2 | 14.0 | 155% | 196% |
| *Lactobacillus casei* ATCC393 | 13.5 | 11.8 | 9.0 | 129% | 203% |
| *Lactobacillus crispatus* ATCC 33820 | 14.0 | 13.1 | 10.4 | 118% | 182% |
| *Lactobacillus delbrueckii* ATCC12315 | 15.6 | 12.9 | 9.8 | 152% | 233% |
| *Lactobacillus fermentum* ATCC14931 | 16.2 | 14.0 | 11.2 | 150% | 215% |
| *Lactobacillus helvaticus* ATCC15009 | 16.2 | 14.1 | 11.0 | 148% | 220% |
| *Lactobacillus paracasei* ATCC25302 | 14.0 | 10.8 | 9.9 | 163% | 195% |
| *Lactobacillus pentosus* ATCC8041 | 15.4 | 12.0 | 10.1 | 168% | 199% |
| *Lactobacillus plantarum* ATCC14917 | 15.5 | 12.0 | 10.1 | 171% | 200% |
| *Lactobacillus reuteri* ATCC23272 | 15.4 | 12.0 | 9.8 | 167% | 201% |
| *Lactobacillus rhamnosus* ATCC7469 | 13.5 | 11.7 | 9.0 | 131% | 204% |
| *Lactococcus lactis* ATCC11454 | 12.6 | 11.3 | 8.9 | 120% | 186% |
| *Strep. thermophilus* ATCC19987 | 12.0 | 11.1 | 8.1 | 116% | 192% |
| AVERAGE VALUES | 15.7 | 13.5 | 11.2 | 143% | 201% |

*Control (LAB inoculum in broth media without any LF) growth is considered as 100%.

EXAMPLE 4

Antioxidant Activity of LF-TCR

The ferric reducing ability of plasma (FRAP) assay (Benzie I F, Strain J J, Ferric reducing antioxidant poser as a measure of antioxidant capacity: the FRAP assay. In: 'Methods in Enzymology: Oxidants and Antioxidants', et. L/Packer, pp15-27, Orlando, Fla., Academic Press, 1999) with minor modifications was used to measure the antioxidant activity of LF and different test compounds. The FRAP reagent was prepared by mixing 40 mL of 0.3 M acetate buffer (pH 3.6), 4 mL of 20 mM ferric chloride and 4 mL of 10 mM TPTZ [2,4,6-Tris(2-pyridyl)-s-triazine]. Serial dilutions (0.1 to 1.0 mM) of 6-OH-2,5,7,8-tetramethylchroman-2-carboxylic acid (CAS 53188-07-1) were used as FRAP standards. All reagents were brought to 37° C. prior to the assay. FRAP assay was performed in a 96-well microplate by mixing 20 µL of deionized (DI) water, 10 µL of test sample (LF, turmeric root extract or ascorbic acid) and 150 µL of FRAP reagent. In combination studies 10 µL of DI water and 20 µl of LF mixtures (with turmeric root extract or ascorbic acid) were mixed with 150 µL of FRAP reagent. After incubation at 37° C. for 5 min (for ascorbic acid) and for 5 min to 24 h (for LF and LF/turmeric combinations), the absorbance of reaction mixtures was measured at 593 nm using a microplate reader (Spectramax 340 PC). Test compounds were given antioxidant (FRAP) scores compared to the FRAP value of ascorbic acid.

Figure 2:
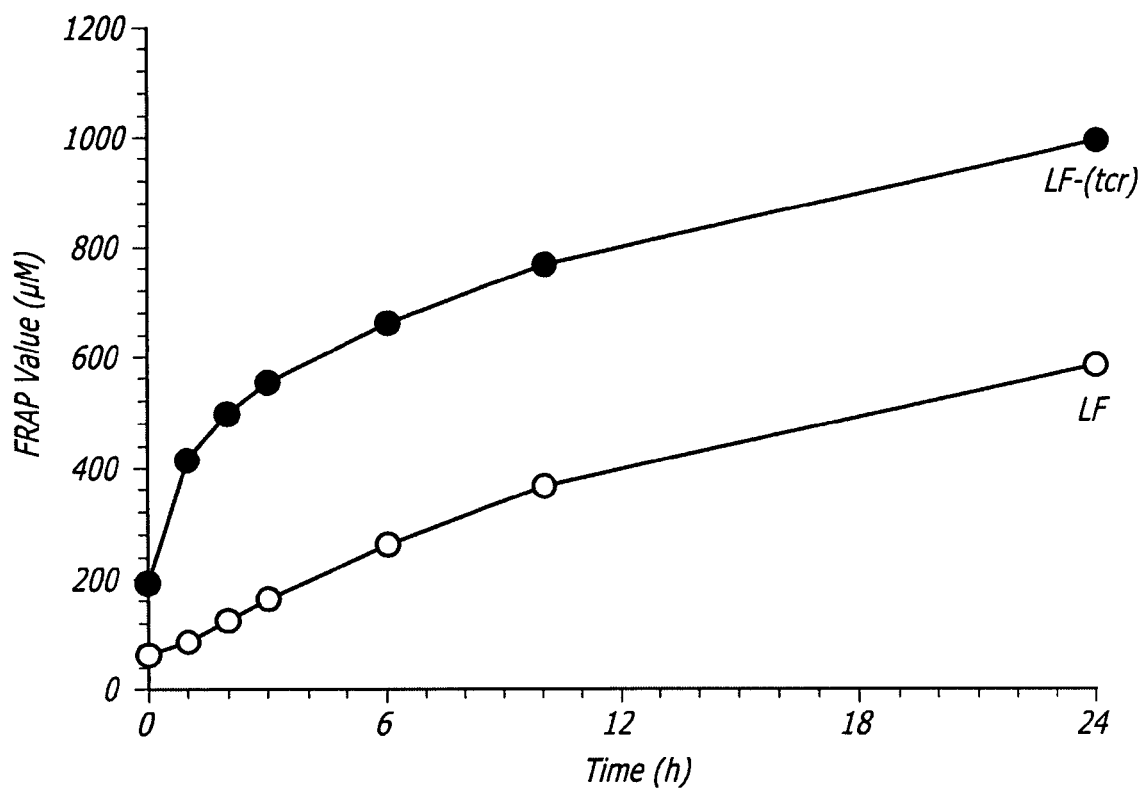
FIG. 2 graphically depicts the antioxidant activity (FRAP units) of commercial LF and LF-TCR after ultra-cleansing according to the teachings of the present invention.

The FRAP reaction kinetics (measured as the rate of increase in absorbance of reaction mixtures at 593 nm) of LF-TCR was compared with that of LF. When tested a 0.1 mM concentration, LF showed an antioxidant activity (FRAP units) with an initial value of 60 with a gradual rise to 260 in 6 h and reached 583 in 24 h. Under similar test conditions, a 0.1 mM concentration of LF-TCR demonstrated an enhanced antioxidant activity starting at 192 FRAP units (3.2× times higher than LF) with an increased activity of 660 (2.5× times higher than LF) at 6 h which peaked to 994 (1.7× times higher than LF) at 24 h. Data graphically depicted in FIG. 2 clearly indicates that the LF-TCR prepared according to the TCR process of the present invention is at least twice potent in antioxidant activity compared to its starting LF raw material.

EXAMPLE 5

Effects of LF-TCR on Eucaryotic Cell Apoptosis

The effects of LF-TCR on Caco2 (colon carcinoma cell line) undergoing apoptosis was tested. The Caco2 cells were grown in Eagle's minimal essential medium (EMEM supplemented with 1% non-essential amino acids and 10% fetal calf serum) in a 8-well tissue culture plate for 72 h in a $CO_2$ incubator. After partial monolayers were obtained, each plate was washed twice with phosphate buffered saline (PBS, pH 7.2). A 2 mL volume of LF-TCR or other test samples diluted in EMEM were added to each well containing approximately $10^5$ Caco2 cells. The proliferation of Caco2 cells and the cytomorphological changes in the monolayer was examined after 24 h and 48 h incubations by the following two methods: i) Annexin V staining, an early marker for dying cells, and ii) Tunel assay, a late marker for dying cells in which the reagent binds to fragmented DNA. Apoptosis was also induced with 1 µM staurosporine treatment for 30 min followed by washing with tissue culture medium. Cells were rinsed with binding buffer three times and further incubated with binding buffer containing 5 µL of Annexin V (Cell Signaling Inc., Beverly, Mass.) for 15 min at room temperature in the dark. Cells were then washed with PBS and fixed in 2% paraformaldehyde in PBS for 15 min at room temperature in the dark. After washing with PBS, cell chambers were removed and slides were mounted in Vectashield® anti-fade solution containing 4', 6-diamidino-2-phenylindole (DAPI). Cells were viewed under Leica (Wetzlar, Germany) DMRA microscope with Plan-apochromat x40/1.25 NA and x63/1.40 NA oil immersion objective lenses. Images were acquired with a SkyVision-2/VDS digital CCD (12-bit, 1280×1024 pixel) camera in unbinned or 2×2-binned models into EasyFISH software, saved as 16-bit monochrome, and merged as 24-bit RGB TIFF images (Applied Spectral Imaging Inc., Carlsbad, Calif.). Cells staining positive with Annexin V indicate that cells were undergoing apoptosis. The number of positive cells were determined per a given field with various treatments and expressed as percent dead cells compared to untreated (control) cells.

Figure 3:
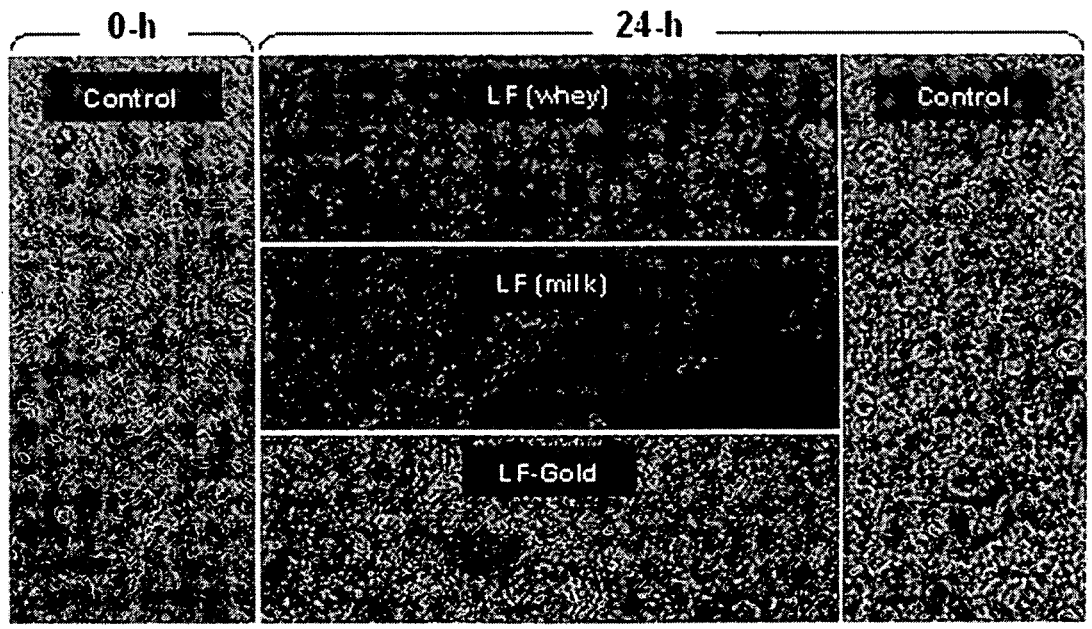
FIG. 3 depicts induction of apoptosis in Caco2 cells after incubation with commercial LF from whey [LF(whey)] or from milk [LF(milk)] or with LF-TCR prepared according to the teachings of the present invention.

In the presence of LF-TCR Caco2 cells showed <1% apoptosis after 24 h incubation. Under similar tissue culture conditions, milk-derived LF and whey-derived LF elicited 35% and 53% apoptosis, respectively. Finally, the untreated Caco2 (control) cells demonstrated 5% apoptosis after 24 h. The results of this study are depicted in FIG. 3. These data indicated that LF-TCR protects intestinal cells from apoptosis, whereas, commercial LF preparations (containing contaminants) could elicit cytotoxicity against Caco2 cells.

EXAMPLE 6

LF-TCR Formulations

In accordance with an embodiment of the present invention, a LF composition is in the form of a multi-layered coated tablet or capsule. If probiotics were included in the mixture, the freeze-dried probiotic LAB were embedded in at least one core of the tablet in the form of granules and at least one shell structure is present containing (fdn)-LF with surfactants including, but not limited to, polysorbates, saponins, and bile salts and endotoxin-neutralizing substances in permissible quantities such as phytochemical antioxidants including, but not limited to, polyphenols, oleoresins, terpenes, flavonoids, phycocyanins and substances adapted to create an anion-rich environment including, but not limited to, carbonates, bicarbonates, carbonated liquids and anaerobic encapsulation systems. The delivery system in accordance with this invention may be in solid, liquid or gel form comprising with or without probiotic LAB.

The LF-TCR of the present invention may be used as a component of compositions including, but not limited to, pharmaceuticals, food additives, nutritional supplements, cosmetic formulations. In one embodiment of the present invention, a pharmaceutical composition of LF-TCR was administered along with a pharmaceutically acceptable excipient or carrier comprising any compatible, non-toxic substance suitable to deliver the LF-TCR to the recipient. Non-limiting examples of pharmaceutically acceptable excipients include, but are not limited to, sterile water, alcohol, fats, waxes, inert solids, adjuvants, buffering agents and dispersing agents. The concentration of the LF-TCR in the pharmaceutical composition can vary widely, i.e., from less than about 0.01% by weight, usually being at least about 1% by weight to as much as 20% by weight or more. Methods for preparing pharmaceutical compositions are well known in the art and described in more detail in various sources, including, for example, Remington's Pharmaceutical Science (15th ed., Mack Publishing, Easton, Pa., 1980) (incorporated by reference in its entirety for all purposes). Table 6 depicts the ingredients in one formulation of a LF-TCR-containing composition. The scope of the present invention contemplates other LF-TCR formulations can be made in accordance with the teachings of the present invention.

For oral administration, LF-TCR can be given in solid dosage forms, such as capsules, tablets and powders, or in liquid dosage forms, such as elixirs, syrups, and suspensions. The LF-TCR compositions of the present invention can be administered with potable water or a foodstuff (eg. milk).

TABLE 6

LF-TCR base formulation for different human in vivo applications

| INGREDIENTS | W/V |
|---|---|
| LF-TCR | 80.0% |
| Turmeric root extract | 10.0% |
| Sodium bicarbonate | 7.5% |
| Vitamin C | 2.5% |
| TOTAL | 100.0% |

Table 6 presents an exemplary embodiment of a LF-TCR formulation of the present invention. The above formulation can be supplemented with appropriate strains of probiotic LAB from $10^6$ to $10^{11}$ CFU/g when required. Additionally, DMSO (at 0.05 to 5%) can be added for enhanced diffusion of the formulation as required. The formulation of Table 6 has been used to prepare LF-TCR-containing compositions in various different forms.

EXAMPLE 7

Dietary Supplement Formulations

TABLE 7

LF-TCR-based dietary supplement formula

| INGREDIENTS | Vitamin A-based | Vitamin C-based |
|---|---|---|
| LF-TCR | 33.3% | 31.6% |
| Turmeric root extract | 16.7% | 15.8% |
| Antioxidant (vitamin A or C) | 11.1% | 15.8% |
| Polysorbate-80 | 2.8% | 2.6% |
| Sodium bicarbonate | 8.3% | 7.9% |
| Fructooligosaccharide (as inulin) | 27.8% | 26.3% |
| Total | 100% (225 mg) | 100% (245 mg) |

A pharmaceutical composition of LF-TCR was prepared with the ingredients listed in Table 7. Appropriate ratios of LF-TCR, turmeric root extract, antioxidant (Vitamin A or C) and inulin were mixed to form Mixture A. Mixture B included a mixture of sodium bicarbonate sprayed with polysorbate-80. Mixtures A and B were then mixed to homogeneity and the composition was encapsulated in hydroxypropylmethyl cellulose (HPMC) two-piece capsules according to methods commonly practiced in the art of manufacturing of dietary supplements.

In vitro testing of the capsules (weight range 225-250 mg) showed a superior cytoprotective effect on Caco2 cells (<1% apoptosis after 24 h exposure), induced a synergistic antioxidant activity (FRAP value =>2.5 mM in 24 h) with the vitamin-turmeric containing composition and a potent prebiotic activity to promote growth of *Lactobacillus acidophilus* (growth increased >245% over control) and *Bifidobacterium bifidum* (>310% over control).

The composition of Example 7 was self-administered by subject A, an adult woman with a long history of rheumatoid arthritis. Over several years subject A had experienced no relief from medications prescribed by physicians. Pain and inflammation of the joints, and mobility improved as soon as a regime was initiated in which two to four capsules of the product were oral administered daily. Over two months the health status improved to the point at which symptoms were considerably diminished.

EXAMPLE 8

LF-TCR-Based Nutritional Drinks

TABLE 8

LF-TCR-based nutritional drink formula

| INGREDIENT | Citrate-based | EDTA-based |
|---|---|---|
| LF-TCR | 29.4% | 28.5% |
| Chelator (citrate or EDTA) | 2.9% | 0.3% |
| Sodium bicarbonate | 5.9% | 11.4% |
| Cranberry extract | 29.4% | 28.5% |
| Grape skin extract | 14.7% | 14.2% |
| Polysorbate-80 | 1.5% | 1.4% |
| D-Ribose | 14.7% | 14.2% |
| Thiamine (B1) | 0.6% | 0.6% |
| Riboflavin (B2) | 0.9% | 0.9% |
| Total | 100% (340 mg) | 100% (351 mg) |

Cranberry extracts suitable for use in the compositions of the present invention include those extracts with superior levels of proanthocyanidins. A non-limiting example of a cranberry extract is NutriCran Bio-100™ (Decas Botanical Synergies, Wareham, Mass.). Grape extracts, including those from the skin or seeds, useful in the compositions of the present invention include those extracts with a high phenolic content with a preferred ration of monomers (10%-15%), oligomers (70%-80%) and polymers (10%-15%). Non-limiting exemplary grape extracts include MegaNatural®GSKE grape skin extract and MegaNatural® gold grape seed extract (from Polyphenolics, Inc., Madera, Calif.).

Pharmaceutically acceptable excipient also contained in the LF-TCR nutritional drink composition include, but are not limited to, fructose-DC (230 mg), magnesium stearate (10 mg), stearic acid (20 mg) with natural cherry flavor and natural red color and all the ingredients were blended to a homogenous mixture. Each dosage of the LF-TCR composition, approximately 600 mg of powdered mixture from Table 8 along with the excipients listed above, was dissolved in 8 fl oz (240 mL) of potable water and subjected for in vitro testing. The nutritional drink showed a cytoprotective effect on Caco2, Hep-2 (human epithelial larynx carcinoma) and uroepithelial cells resulting in <1%, <1% and <5% apoptosis after 24 h exposure, respectively. This LF-TCR formulation containing cranberry extract and grape skin extract induced a synergistic antioxidant activity (FRAP value=>2.1 mM in 24 h), induced prebiotic effects by promoted the growth of *Lactobacillus crispatus* (>150% increase growth over control) and effectively inhibited the interaction of p-fimbriated *E. Coli* with uroepithelial cells.

The composition of Example 8 was self-administered by subject B, an adult patient with an acute urinary tract infection with gentamycin-resistant p-fimbriated *E. coli*. The leukocyte count in the urine declined soon after the regime was initiated in which four to five doses of product were dissolved in potable water and oral consumed daily. In two days the symptoms subsided and the microbiological culture indicated a total absence of *E. coli* from the urine of the patient.

EXAMPLE 9

LF-TCR Chewable Tablets

TABLE 9

LF-TCR-based chewable tablet formulation

| INGREDIENT | Vitamin A-based | Vitamin C-based |
|---|---|---|
| LF-TCR | 33.3% | 31.2% |
| Antioxidant (Vitamin A or C) | 6.7% | 12.5% |
| Sodium bicarbonate | 6.7% | 6.2% |
| Polysorbate-80 | 1.7% | 1.7% |
| Lysozyme | 8.3% | 7.8% |
| Lactoperoxidase | 8.3% | 7.8% |
| Xylitol | 33.3% | 31.2% |
| Zinc oxide | 1.5% | 1.4% |
| Peppermint oil | 0.2% | 0.2% |
| Total | 100% (300 mg) | 100% (320 mg) |

Pharmaceutically acceptable excipients including fructose-DC, magnesium stearate, stearic acid, CanTab (tableting dextrose, Penford Food Ingredients, Englewood, Colo.), natural cherry flavor and natural blue color were blended with the ingredients from Table 9. Each of the above ingredients was placed, in powdered form, into a commercial mixer, mixed and, if necessary, passed through a mesh screen to remove aggregates. After 20 minutes of thorough mixing, the composition was cold pressed in a tablet press set at a maximum pressure of 6.4 tons yielding chewable tablets of 1500 mg weight and hardness of 34 to 36 Kp (kilopond).

EXAMPLE 10

Mouthwash with LF-TCR

A mouthwash base was prepared by combining cetylpyridinium chloride (1 g), citric acid USP (1 g) and sweetner (q.s), dissolving in 100 mL deionized water and mixing with 100 mL alcohol USP. Flavor oils (peppermint, eucalyptus and clove oils; 1.5 mL) were mixed with polyoxyethylene [20] sorbitan monostearate (3.0 g) and this blend was slowly added to the hydroalcoholic solution while stirring. A 70% sorbitol solution (200 g) was added and the volume made up to 1000 mL with deionized water. In one embodiment of the present invention, the LF-TCR formulation of Table 6 and mouthwash base were mixed to homogeneity at 1:10 ratios.

EXAMPLE 11

Vaginal Healthcare Formulations

The preparation of vaginal suppository compositions includes well known techniques of rolling (hand shaping), molding (fusion) and cold compression. Suppositories are usually globular or oviform and weigh about 5 grams. Reference is made to Remington's Pharmaceutical Sciences, 18th Edition, Chapter 87, pages 1609-13 (1990), the disclosure of which is expressly incorporated herein by reference.

Preparation of a vaginal suppository containing the LF-TCR formulation of Table 6 can be prepared as described above in accordance with well known techniques in the art. In a typical suppository formulation, the active agents are combined with an appropriate pharmaceutically acceptable suppository base such as cocoa butter, esterified fatty acids, glycerinated gelatin, and various water-soluble or dispersible bases like polyethylene glycols and polyoxyethylene sorbitan fatty acid esters. Various additives, enhancers, or surfactants may be incorporated.

Such suppositories will generally be constructed of a mixture of substances that are solid at room temperature but melt at body temperature. The substances commonly used to create such vehicles include, but are not limited to, theobroma oil, glycerinated gelatin, hydrogenated vegetable oils, mixtures of polyethylene glycols of various molecular weighty and fatty acid esters of polyethylene glycol.

Additionally, vaginal suppository compositions may include a water soluble base. A water soluble base lowers the surface tension of the composition aiding in a more thorough distribution. A water soluble base also decreases the risk of secondary infection. Illustrative water soluble bases include, but are not limited to, corn starch, aloe and cocoa butter.

The vaginal suppository compositions of the present invention may also include propylene glycol. Propylene glycol acts as a surfactant and assists in penetration, contact, and absorption of the active ingredients. Propylene glycol also serves as a preservative and as an antimicrobial agent.

The vaginal suppository compositions of the present invention may also include a non-ionic surfactant such as polysorbate. Such a surfactant provides better surface contact of the composition with the vaginal mucosa by further reducing surface tension.

The vaginal suppository compositions of the present invention may also be formulated in combination with other drugs, such as spermicides, antibiotics (antibacterials, antifungals, antivirals and antiparasitics) and anti-inflammatory agents, thereby further broadening the composition's medical efficacy.

The vaginal suppository compositions of the present invention may also be pH balanced by the addition of a base including, but not limited to, triethanolamine, sodium hydroxide and sodium bicarbonate to adjust the pH to a level compatible with the tissue being treated. In the normal vagina, the pH is between approximately 3.8-4.4. A humectant may also be included in the composition of the present invention, such as glycerin, to soothe the area being treated, for example, in cleansing solution compositions.

The composition of the present invention may also include a topical anesthetic including, but not limited to, lidocaine hydrochloride and topical steroids including, but not limited to, corticosteroids, to provide relief from pain or itching during treatment.

As will be understood by those skilled in the art, the regimen for treating vaginal infection will depend on the severity of the infection and the form of the composition. By way of a non-limiting example, where the composition is in the form of a cream, the cream is topically applied to the affected area. Where the composition is in the form of a suppository, the suppository is inserted into the vagina, in a non-limiting example, once or twice daily for 7 days.

Terms used herein are to be given their usual meaning in the art unless otherwise stated. The term "vaginal infection" means any vaginal infection of, bacterial, fungal or parasitic origin. Examples of some of the microorganisms which cause such infections include, but are not limited to, microorganisms of the genus *Candida*, particularly *C. albicans, C. tropicalis* and *C. glabrata, Gardneralla vaginalis*, various mixed anaerobic bacteria and *Peptostreptococcus* bacteria.

One vaginal suppository composition including LF-TCR was formulated as described below. In a non-limiting exemplary embodiment of the present invention, the LF-TCR formulation of Table 6 (250 mg) was combined with hydrogen peroxide-producing *Lactobacillus crispatus* ($10^9$ CFU/ dose) together with an active lactoperoxidase system comprised of either Mixture (A) containing lactoperoxidase (1000 IU), urate oxidase (5000 IU), urate (500 mg) and potassium thiocyante (5 mg); or Mixture (B) containing lactoperoxidase (2000 IU), sodium thiocyanate (10 mg) and benzylalkonium chloride (10 µg). Finally, DMSO (0.1% final concentration) was incorporated.

Treatment of the vaginal infection may vary depending on the severity of the infection and appropriate treatment regimens are known to those medical practitioners, particularly gynecologists. An exemplary, non-limiting treatment regimen involves inserting an LF-TCR-containing suppository into the vagina twice daily for 7 days.

Douche solutions containing LF-TCR can be prepared and can optionally contain other ingredients including those typically found in vaginal douches including, but not limited to, antimicrobial agents, anaesthetics or antipruitics (such as phenol or menthol), astringents, surface active agents, propylene glycol, glycerin USP and Polysorbate 20 (Liposorb L20). The solution may be initially formed as a concentrated liquid, dissolvable powder or tablet. When use is desired, water may be added, preferably warm in temperature, to produce a solution of desired concentration.

EXAMPLE 12

Skin and Wound Care Formulations of LF-TCR

The term skin condition can refer to any skin condition which results from bacterial, parasitic, fungal, insecticidal and actinomycotic infection and includes keratinization disorders. Non-limiting examples of microorganisms which can cause such infections include *Candidia albicans*, microorganisms of the genera *Trichophyton, Epidermophyton* and *Microsporum*, parasites such as *Sarcoptes scabieii, Streptotrichosis*, various dermatophytes, various types of ectoparasites and insects, for example, fleas, lice and mites.

The term effective amount refers to an amount of a composition which is effective in treating a particular infection and is determinable by a person of skill in the art such as a medical practitioner.

For wound healing, the LF-TCR formula is preferably applied repeatedly from the time the wound first occurs. Preferably, the LF-TCR composition is applied at least about every time the wound dressing is changed. The LF-TCR composition can also be applied at least about every other day, more preferably, every day.

Numerous administration vehicles will be apparent to those of ordinary skill in the art including, without limitation, slow release formulations, liposomal formulations and polymeric matrices.

Preparation of each of the formulations described herein would be within the knowledge of the person of skill in the art, although reference is made to Remington's Pharmaceutical Sciences, 18th Edition (1990), the disclosure of which is expressly incorporated herein by reference.

In a non-limiting example of a skin or wound care formulation, a medicated ointment base was prepared with ingredients (% w/v) as follows: Base (A) contained mineral oil USP (25%), microcrystalline wax (10%), cetyl alcohol (5%), mixed lanolin alcohols (10%), sorbitan sesquioleate, (3%) and propyl p-(OH)-benzoate (0.1%). Base (B) contained glycerine (3%), methyl p-(OH)-benzoate (0.1%) and deionized water (43.8%). Bases (A) and (B) were heated separately to 75° C. and mixed with gentle stirring while cooling to 45° C. to prepare the ointment base. In an exemplary embodiment of the present invention, the LF- TCR formulation of Table 6 and the ointment base were mixed to homogeneity at 1:5 ratios.

In a non-limiting example of a skin or wound care formulation, a skin cleansing solution composition was prepared. The base solution formula was as follows, in which the percentages are given as % w/w of the total composition: water (81%), propylene glycol (5%), glycerin USP (5%), and polysorbate-20 (5%). The LF-TCR formulation of Table 6 (5% w/v final concentration) was mixed in slowly until completely dissolved. The mixed solution was uniform and clear. The solution may be further diluted by the addition of water. The LF-TCR skin cleansing solution can be applied to the infected area of the skin by any suitable means such as cotton wool, cotton swab or the like.

In a non-limiting example of a skin or wound care formulation, a mild non-irritating skin crème base was prepared as follows: Oil phase(A) consisted of cetearly alcohol (5%), silicone oil 200 fluid (1%), isopropyl myristate (2%) and sodium stearoyl-2-lactylate (2%). Aqueous phase (B) consisted of propylene glycol (5%), sodium citrate (0.2%) and purified water to make up to 100% w/v. The components of oil phase (A) were combined at 65° C. The components of aqueous phase (B) were combined at 70° C. Aqueous phase (B) was added to oil phase (A) under cooling with moderate agitation. In an exemplary embodiment of the present invention, the LF-TCR formulation of Table 6 and the ointment base were mixed to homogeneity at a 1:10 ratio.

In a non-limiting example of a skin or wound care formulation, a makeup crème base was prepared as following: Mixture (A) contained magnesium aluminium silicate (2.6%), sodium carboxymethyl cellulose (0.4%) and deionized water (42.4%). Mixture (B) contained a dispersing agent (0.3%), propylene glycol (5.0%) and deionized water (12.3%). Mixture (C) contained talc (18.5%), kaolin (1.3%), titanium dioxide (3.7%) and iron oxides, (1.5%). Mixture (D) contained isopropyl myristate (5.0%), strearyl alcohol (2.0%), lanolin absorption base (2.0%), sorbitan monolaurate (0.75%), polyoxyethylene (20) sorbitan monolaurate (2.25%) and perfume. Solids of (A) were blended, added to water at 80° C. and stirred until smooth. Contents of (C) were pulverized and added to (B) and passed through a colloid mill to yield smooth paste. Mixture (B)+(C) was added to (A) and heated to 60-65° C. The contents of (D) were then heated to 70° C. and mixed with the (A)+(B)+(C) blend; stirred until the temperature reached 45° C., perfume was added and mixed until cool. In an exemplary embodiment of the present invention, the LF-TCR formulation of Table 6 and the makeup crème base were mixed to homogeneity at a 1:10 ratio.

In a non-limiting example of a skin or wound care formulation, an antiperspirant base was prepared as follows: Oil phase (A) was prepared with mineral oil (23%), calcium stearoyl-2-lactylate (3.2%) and PEG 400 dioleate, (0.8%). Aqueous phase (B) contained glycerine (3%), 60% sodium lactate (10%) and purified water (20%). Mixture (C) was 50% aluminum chlorohydrate (40%). Mixtures (A), (B) and (C) were heated separately at 70° C. Aqueous phase solution (B) was quickly added to (C) followed by mixing of (A) with moderate agitation while cooling. In an exemplary embodiment of the present invention, the LF-TCR formulation of Table 6 and the antiperspirant base were mixed to homogeneity at a 1:10 ratio.

EXAMPLE 13

LF-TCR Containing Shampoo

A non-limiting example of a composition containing an LF-TCR formulation made according to the teachings of the present invention is a shampoo. The shampoo composition comprised: water (59.3-66.1%), alpha-olefin sulfonate (20-23%), lauramide DEA (0.8-1%), cocamidopropyl betaine (6-8%), fragrance (0.27%), glycerin USP (0.5%), safflower oil (0.003%), Kathon™ CG (0.1%), and sodium lactate (1-2%) in which the percentages are given as % w/w of the total composition. Methocel™ F4m (0.2-0.3%) and Glucamate™ DOE 120 (1.0-1.5%) were then added slowly and mixed until uniform and completely free of lumps. The LF-TCR formulation (10% w/v final concentration) of Table 6 was then added and the mixture stirred to homogeneity.

The shampoo can be used by massaging a suitable amount, such as about 5 mL of the shampoo into the hair and/or body and rinsing off with warm water.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

I claim:

1. A therapeutic lactoferrin composition comprising:
   lactoferrin purified by the method of treatment for contaminant reduction (LF-TCR), said method comprising the steps of:
   1) treating said commercial lactoferrin preparation with at least one surfactant;
   2) contacting said surfactant-treated lactoferrin with at least one antioxidant;
   3) purifying said antioxidant-treated lactoferrin with at least one polyphenol to form purified lactoferrin; and
   4) diving said purified lactoferrin;
   said therapeutic composition further comprising at least one surfactant;
   at least one antioxidant;
   at least one polyphenol; and
   at least one anionic compound;
   wherein microbial load and endotoxin activity in said lactoferrin have been eliminated.

2. The therapeutic lactoferrin composition of claim 1 wherein said at least one surfactant is selected from the group consisting of food-grade detergents, bile salts and plant saponins.

3. The therapeutic lactoferrin composition of claim 1 wherein said at least one antioxidant is selected from the group consisting of Vitamin A, Vitamin C, Vitamin E and metal chelators.

4. The therapeutic lactoferrin composition of claim 1 wherein said at least one polyphenol is selected from the group consisting of oleoresins, terpenes, flavonoids and biliproteins.

5. The therapeutic lactoferrin composition of claim 1 wherein said at least one anionic compound is selected from the group consisting of carbonates, bicarbonates or carbonated liquids.

6. The therapeutic lactoferrin composition of claim 1 wherein the daily dosage of lactoferrin is between approximately 0.01 and 10,000.00 mg.

7. The therapeutic lactoferrin composition of claim 1 wherein said therapeutic lactoferrin composition is delivered to a tissue/mucosal site of a recipient in need thereof.

8. The therapeutic lactoferrin composition of claim 7 wherein said tissue/mucosal site is selected from the group consisting of the gastrointestinal tract, the oropharyngeal region, the nasopharyngeal region, the vulvo-vaginal region and the skin.

9. The therapeutic lactoferrin composition of claim 1 wherein said therapeutic lactoferrin composition comprises a pharmaceutical formulation selected from the group consisting of tablets, capsules, powders, drinks, chewable tablets, mouthwashes, suppositories, douches, ointments, skin cleansing solutions, crèmes, makeup, antiperspirants and shampoos.

10. A therapeutic lactoferrin composition comprising:
   lactoferrin purified by the method of treatment for contaminant reduction (LF-TCR) wherein microbial load and endotoxin activity in said lactoferrin have been eliminated said method comprising the steps of:
   1) treating said commercial lactoferrin preparation with at least one surfactant;
   2) contacting said surfactant-treated lactoferrin with at least one antioxidant;
   3) purifying said antioxidant-treated lactoferrin with at least one polyphenol to form purified lactoferrin; and
   4) drying said purified lactoferrin.

* * * * *

UNITED STATES PATENT AND TRADEMARK OFFICE
CERTIFICATE OF CORRECTION

PATENT NO. : 7,326,775 B2 Page 1 of 1
APPLICATION NO. : 11/293565
DATED : February 5, 2008
INVENTOR(S) : A. Satyanarayan Naidu It is certified that error appears in the above-identified patent and that said Letters Patent is hereby corrected as shown below:

On the Title Page Item (75) Inventor: A. "Satanarayan" Naidu should be spelled A. --Satyanarayan-- Naidu Signed and Sealed this Twenty-seventh Day of May, 2008

JON W. DUDAS
*Director of the United States Patent and Trademark Office*